US007058658B2

(12) United States Patent
Mentzer

(10) Patent No.: US 7,058,658 B2
(45) Date of Patent: Jun. 6, 2006

(54) MOLECULAR DATABASE FOR ANTIBODY CHARACTERIZATION

(75) Inventor: Steven Mentzer, Boston, MA (US)

(73) Assignee: Dana-Farber Cancer Institute, Inc., Boston, MA (US)

( * ) Notice: Subject to any disclaimer, the term of this patent is extended or adjusted under 35 U.S.C. 154(b) by 384 days.

(21) Appl. No.: 09/819,939

(22) Filed: Mar. 28, 2001

(65) Prior Publication Data

US 2001/0049689 A1    Dec. 6, 2001

Related U.S. Application Data

(60) Provisional application No. 60/193,353, filed on Mar. 28, 2000.

(51) Int. Cl.
    *G06F 17/00* (2006.01)
(52) U.S. Cl. .................................. 707/104.1; 435/6
(58) Field of Classification Search ................ 707/3, 707/5, 104.1, 10; 715/533; 382/129, 133; 348/79, 135; 530/324, 326; 356/39; 436/546; 435/6
    See application file for complete search history.

(56) References Cited

U.S. PATENT DOCUMENTS

| 4,741,043 | A | * | 4/1988 | Bacus ..................... 382/129 |
| 4,870,568 | A | * | 9/1989 | Kahle et al. ................. 707/5 |
| 5,196,510 | A | * | 3/1993 | Rodwell et al. ............. 530/324 |
| 5,487,112 | A | * | 1/1996 | Zygourakis et al. ........ 382/133 |
| 5,596,703 | A | * | 1/1997 | Eick et al. .................. 345/700 |
| 5,627,040 | A | | 5/1997 | Bierre et al. ................ 435/24 |
| 6,115,708 | A | | 9/2000 | Fayyad et al. ................ 707/6 |
| 6,344,319 | B1 | * | 2/2002 | Bensimon et al. ............ 435/6 |
| 2002/0015971 | A1 | * | 2/2002 | Verwer .................... 435/7.24 |
| 2003/0028501 | A1 | * | 2/2003 | Balaban et al. .............. 707/1 |

FOREIGN PATENT DOCUMENTS

| WO | WO97/29212 | 8/1997 |
| WO | WO 01/18735 | 3/2001 |

OTHER PUBLICATIONS

Hardle, Marron, and Wand; Bandwidth Choice for Density Derivatives; 1990; pp. 223 to 232.
Wand, Marron, and Ruppert; Transformations in Density Estimation; 1991; pp. 343 to 361.
Wand; Finite sample performance of density estimators under moving average dependence; 1990; Rev. 1991; pp. 109-115.

(Continued)

*Primary Examiner*—Mohammad Ali
*Assistant Examiner*—Etienne P LeRoux
(74) *Attorney, Agent, or Firm*—Palmer & Dodge, LLP

(57) ABSTRACT

The invention relates to a cumulative, evolving molecular database of monospecific probes and their characteristics. In particular, the invention relates to a computer repository of histograms based upon quantitative flow cytometry. The invention further relates to a system containing a database of monospecific probe properties, the database connected to users through a network to allow users to enter selection criteria and retrieve monospecific probe properties. The invention further relates to a data set useful to refine existing analytic algorithms. The refinement of these algorithms enables computer searches for relationships between known and unknown monospecific probes. Thus, the invention also provides for searching in the database to identify relationships between monospecific probes, groups of probes, and their targets.

13 Claims, 13 Drawing Sheets

OTHER PUBLICATIONS

Wand and Jones; Comparison of Smoothing Parameterizations in Bivariate Kernel Density Estimation; 1993; pp. 520 to 528.

Wand and Devroye; How easy is a given density to estimate; Jan. 1992; Rev. Jun. 1992; pp. 311 to 323.

Wand; Fast Computation of Multivariate Kernal Estimators; 1994; pp. 433 to 445.

Wand and Jones; Multivariate Plug-in Bandwidth Selection; 1994; pp. 97 to 115.

Gilbert; Aldershof, Marron, Park, and Wand; Facts About the Gaussian Probability Density Function; 1995; pp. 289 to 306.

Fan, Heckman, and Wand; Local Polynornial Kernel Regression for Generalized Linear Models and Quasi-Likelihood Functions; 1995; pp. 141 to 144.

Ruppert, Sheather, and Wand; An Effective Bandwidth Selector for Local Least Squares Regression; 1995; pp. 1257 to 1270.

Hall and Wand; On the Accuracy of Binned Kernel Density Estimators; 1996; pp. 165 to 184.

Carroll, Fan, Gijbels, and Wand; Generalized Partially Linear Single-Index Models; 1997; pp. 477 to 489.

Wand, Statistical Computing and Graphics/Data-Based Choice of Histogram Bin Width; 1997; pp. 59 to 64.

Greenes; Strategic Planning Activities of the American Medical Informatics Association; 1994; pp. 263 to 271.

Greenes and Deibel; Collaborative health Care Information System Development Through Sharable Infrastructure, Services, and Paradigms; 1995; pp. 190 to 194.

Shortliffe, Barnett, Cimino, Greenes, Huff, and Patel; Collaborative Medical Informatics Research Using the Internet and the World Wide Web; 1996; pp. 125 to 129.

Greenes, Boxwala, and Ohno-Machado; The Decision Systems Group: Creating a Framework for Decision Making; Jul./Aug. 1999; pp. 23 to 27.

Kaufman, Shortliffe, and Greenes; Toward a Framework for Computer-Mediated Collaborative Design in Medical Informatics; 1999; pp. 158 to 176.

Shortliffe, Patel, Cimino, Barnett and Greenes; A study of collaboration among medical informatics research laboratories; 1998; pp. 97 to 123.

Zeng and Cimino; Evaluation of System to Identify Relevant patient Information and its Impact on Clinical Information Retrieval; 1999; pp. 642 to 646.

Zeng; and Cimino; Automated Knowledge Extraction from the UMLS; 1998; pp. 568 to 572.

Cimino, Elhanan, and Zeng; Supporting Infobuttons with Terminological Knowledge; 1997; 528 to 532.

Hopkins, Ross, and Dutia; Summary of workshop findings of leukocyte antigens in sheep; 1993; p. 49 to 59.

Dutia, Ross, and Hopkins; Comparison of workshop CD45R monoclonal antibodies with OvCD45R monoclonal antibodies in sheep; 1993; pp. 121 to 128.

Hopkins; Workshop studies on the ovine CD4 homologue; 1991; pp. 101 to 102.

Hopkins and Dutia; Workshop studies on the ovine CD1 homologue; 1991; pp. 97 to 99.

Li, Rawn, DeCAmp and Menzer; Hybridoma Screening for Cell Adhesion Molecules Using Multiple Parallel Comparisons in Conditions of Flow; 1996; pp. 43 to 47.

Cobbold; Human Leukocyte Differetiation antigens: Monoclonal Antibody Computer Databases as a Tool for the Future; 1987; pp. 61 to 72.

Benson, Karsch-Mizrachi, Lipman, Ostell, Rapp and Wheeler; GenBank; pp. 15-18.

Saalmuller, Pauly, Aasted, Jenson, Sachs, Arn, Davis, Park, McCullough, Summerfield, Murtaugh, Pampusch, Burger, Laber, Nielsen, Pescovitz, Stokes, Haverson, Boyd and Lunney; Summary of the First Round Analyses of the Second International Swine CD Workshop; pp. 237 to 249.

Valet and Hoffkes; Automated Classification of Patients with Chronic Lymphocytic Leukemia and Immunocytoma From Flow Cytometric Three Color Immunophenotypes; pp. 275 to 288.

Hein, Dudler, Marston, Hopkins, Dutia, Keech, Brandon, and Mackay; Summary of workshop findings for leukocyte antigens of sheep; 1991; pp. 28 to 30.

Ruppert; Local Polynomial Variance-Function Estimation; 1997; pp. 262 to 273.

Hall and Wand; On Nonparametric Discrimination Using Density Differences; 1988; pp. 541-547.

International Search Report.

Benson, et al., (2000) "GenBank", Nucleic Acids Research, vol. 28, No. 1, pp. 15-18.

Cobbold, S. (1987) "Human Leukocyte Differentiation Antigens: Monoclonal Antibody Computer Databases as a Tool for the Future", Molecular and Cellular Probes, vol. 1, pp. 61-72.

Valet, et al. (1997) "Automated Classification of Patients with Chronic Lymphocytic Leukemia and Immunocytoma from Flow Cytometric Three-Color Immunophenotypes", Cytometry, vol. 30, pp. 275-288.

Schuette, et al. (1986) "Count-Dependent Filter for Smoothing Bivariate FCM Histograms", Cytometry, vol. 7, pp. 274-280.

Baxter, et al. (1997) "Some Archaeological Applications of Kernel Density Estimates", Journal of Archaeological Science, vol. 24, No. 4, pp. 347-354.

Copy of International Search Report (EP01970506).

Schuette, et al. "Count-Dependent Filter for Smoothing Bivariate FCM Histograms", Cytometry 1986 vol. 7, pp. 274-280.

Copy of International Search Report (PCT/US01/09908.

* cited by examiner

| | Molecular subunits | Histogram matching |
|---|---|---|
| Cell type 1 | α1β1 | Identical |
| Cell type 2 | α1β1 | Identical |
| Cell type 3 | α2β1 | Discordant |

$$\frac{1}{nh}\sum_{i=1}^{n}K\left(\frac{x_i-x}{h}\right)$$

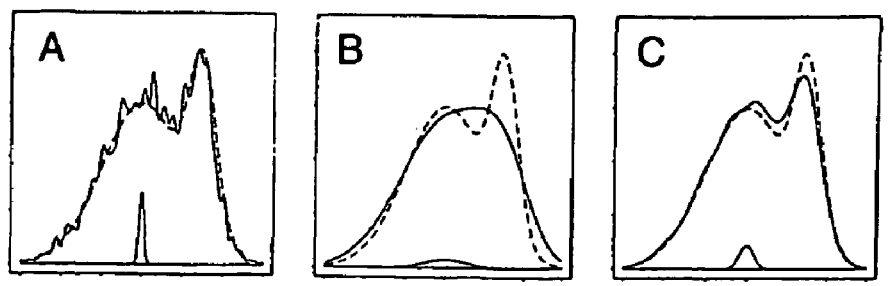
FIGURE 17
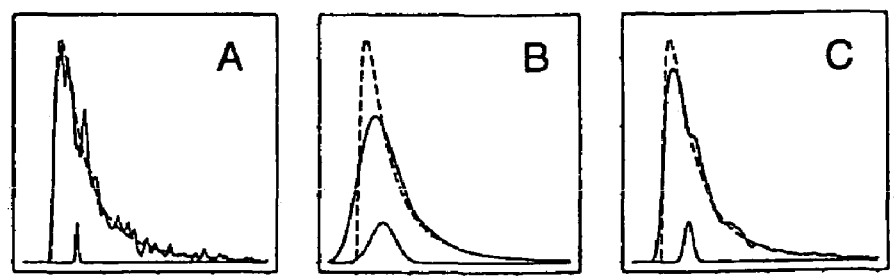
FIGURE 18
$$\frac{1}{nh}\sum_{i=1}^{M} K\left(\frac{g^i - x}{h}\right) c_i \quad (1)$$
FIGURE 19

$$K'(u) = \frac{d}{du}K(u)$$

FIGURE 20

$$\frac{-1}{nh^2}\sum_{i=1}^{M} K\left(\frac{g_i - x}{h}\right)c_i$$

FIGURE 21

$$\frac{1}{nh^3}\sum_{i=1}^{M} K''\left(\frac{g_i - x}{h}\right)$$

MOLECULAR DATABASE FOR ANTIBODY CHARACTERIZATION

PRIORITY

This applications claims priority to the U.S. Provisional Application 60/193,353, filed Mar. 28, 2000.

FIELD OF INVENTION

The present invention relates to the field of molecular databases.

BACKGROUND ART

Monospecific probes, of which monoclonal antibodies (Mab) are an example, have specific reactivity and are biochemically versatile. Such probes have become invaluable tools in such diverse fields as protein chemistry, gene cloning, and clinical therapeutics. A major obstacle to the further development of monospecific probes such as Mabs, however, is the characterization of monospecific probe reactivity. Because the generation of Mabs depends upon complex biologic processes, the characterization of novel Mabs recognizing cell membrane molecules can be unpredictable, expensive, and time-consuming. The problem is further compounded by the absence of established typing cell lines in nonhuman species. The result, at least for Mabs, is that fewer Mab are being developed.

Leukocyte Differentiation Antigen Database Workshops have made a significant contribution to biomedical research over the past 20 years. The workshops have not only created a common molecular language (CD nomenclature), but the common workshop database has reconciled seemingly unrelated molecular observations in far-ranging scientific fields. The workshops were designed to enlist multiple laboratories for flow cytometry analysis. As was observed in a recent Experimental Biology meeting, the workshops are "one of the great contributions of collaborative science in the past 50 years."

The Leukocyte Differentiation Antigen Database workshop approach, however, has two major limitations. First, this approach encourages broad participation, but it precludes the use of rigorous quantitative flow cytometry techniques. The ultimate depth of the data for comparative and predictive purposes is limited due to the variation inherent in data compiled from multiple independent sources. Second, the "cluster method" of data analysis used in the workshops was designed primarily for "typing" cell lines. The use of cell lines typically provides binary results: that is, the cell line is either positive or negative for the expression of the antigen of interest. This approach is less applicable to nonhuman species with few well-characterized cell lines. In most species, membrane molecules must be characterized using cell populations that produce complex histograms.

Because there is no molecular "gold standard," each newly developed monospecific probe must be assessed relative to comparisons with numerous other mono specific probes with similar reactivity. These labor-intensive comparisons are only feasible for a handful of investigators. Alternatively, the investigator can wait to submit the monospecific probe to the next workshop. Because of the complex organization of these workshops, a typical waiting time to submit an antibody can be several years. Perhaps the most worrisome trend is that fewer and fewer monospecific probes are being produced. The most commonly cited reasons are 1) the extraordinary time and effort required for antibody characterization, 2) the possibility that the antigen can not be adequately characterized, and 3) the understandable reluctance of investigators to use partially characterized monospecific probes in their work.

The invention provides a way to overcome these disadvantages and is applicable not only to monoclonal antibodies, but to any monospecific probe.

SUMMARY OF THE INVENTION

The invention provides a molecular database useful for characterizing monospecific probes and probe specificity, and for storing information on monospecific probes and retrieving information for both previously known probes and for new probes.

The invention encompasses a cumulative molecular database of monospecific probes and their characteristics. In particular, the invention provides a repository of information as to monospecific probes, including but not limited to a repository of histograms based upon quantitative flow cytometry.

The invention also provides for storage of information; that is, monospecific probes are processed and the data are posted into a database.

The invention also provides for retrieval of the stored information.

The invention also provides a data set that is useful to refine the existing analytic algorithms using a manageable database. The refinement of these algorithms will enable computer searches for relationships between known and unknown monospecific probes. Thus, the invention also provides for searching in the database to identify common characteristics of previously known and new monospecific probes.

The invention encompasses a system allowing users to obtain information on monospecific probes in an online directory comprising: a web site containing a database of monospecific probe properties and connected to users through a computer network to allow users to enter selection criteria for retrieving monospecific probe properties; wherein the web site produces a list of matching information on monospecific probes matching the selection criteria and displays the matching information on monospecific probes on the list in an order determined by each matching probe's similarity to the selection criteria.

In one embodiment, information in the database comprises monospecific probe histograms.

In a preferred embodiment, the histogram features such as peak location, valley and inflection point location, ascending and descending slopes, and distribution dispersion will be calculated. Feature assessment is facilitated by kernel smoothing to obtain a kernel density estimate.

In another embodiment, the order is determined by a technique selected from the group consisting of a feature (vector) space model, relevance feedback, set training, and performance measurement. Common terminology refers to a vector space model; the term "feature space model" is preferred herein because it is histogram features that are being modeled.

The invention further encompasses a method of providing information concerning monospecific probes to users through a web site, comprising the steps of: receiving information relating a monospecific probe from a user; comparing the information to a monospecific probe information database; compiling a list of matching monospecific probe information matching the information relating to a mono specific probe received from a user; and displaying the matching monospecific probe information in an order determined by similarity of the information relating to a monospecific probe from a user to the monospecific probe information in the database.

In one embodiment, the information in the database comprises histograms.

In another embodiment, the method further includes the steps of receiving a monospecific probe from a user and generating a histogram for the received monospecific probe by the same flow cytometer as the histograms generated for the monospecific probe whose information is contained in the information database.

In a preferred embodiment, the histogram of the monospecific probe received from a user and the histograms of the monospecific probes contained in the database are subjected to kernel smoothing or kernel density estimation before comparison.

The invention further encompasses a directory computer that permits users to obtain a list of monospecific probes matching selection criteria provided by the users through a web site hosted on the directory computer, wherein the directory computer displays matching monospecific probes matching the selection criteria in an order determined by each matching monospecific probe's similarity to the selection criteria.

In one embodiment, the selection criteria is similarity of histograms.

In a preferred embodiment, the histograms have been subjected to kernel smoothing or kernel density estimation.

In another preferred embodiment, the order is determined by a technique selected from the group consisting of a vector space model, relevance feedback, training set, and performance measurement.

The invention further encompasses a computer readable medium having stored thereon computer-executable instructions for: receiving selection criteria relating to information on a monospecific probe from a user; compiling a list of matching monospecific probes matching the selection criteria from a database of monospecific probe information; and displaying the matching monospecific probe information in an order determined by each matching monospecific probe's similarity to the selection criteria.

In one embodiment, the information in the database comprises monospecific probe histograms.

In a preferred embodiment, the histograms have been subjected to kernel smoothing or kernel density estimation.

In another preferred embodiment, the order is determined by a technique selected from the group consisting of a vector space model, relevance feedback, training set, and performance measurement.

The invention further encompasses a method of comparing two mono specific probe histograms comprising the steps of: analyzing a first histogram by kernel smoothing or kernel density estimation; analyzing a second histogram by kernel smoothing or kernel density estimation; and comparing the analyzed histograms.

As used herein, the term "monospecific probe" refers to an entity that specifically binds a single distinct moiety of a given chemical structure or molecule. Monospecific probes encompass, but are not limited to monoclonal antibodies, which bind a specific antigenic epitope. According to the invention the moiety or the molecule comprising a moiety that is bound by a monospecific probe can be known or unknown. For example, a monoclonal antibody can have a known specificity for an epitope on a known cell surface protein, or it can have a binding specificity for an unknown cell surface protein or other protein.

As used herein, the term "single parameter histogram" refers to a plot of data obtained in a flow cytometry analysis measuring the fluorescent labeling intensity of a single moiety on a population of cells by binding of a fluorescently labeled monospecific probe for that moiety.

As used herein, the term "negative control distribution" refers to the area on a histogram showing the fluorescence signal of probes included in a flow cytometry run as negative controls. As used herein, the term "positive control distribution" refers to the area on a histogram showing the fluorescence signal of probes included in a flow cytometry run as positive controls.

As used herein, the term "monospecific probe properties" refers to the collection of characteristics that define a mono specific probe. Examples of "monospecific probe properties" include, but are not limited to the name of the probe within the database, the species of the probe's binding target, the molecular weight of the probe's binding target, the probe's target binding affinity, the cell type or types on which or in which the target is expressed or otherwise localized, isotype (for an antibody), flow cytometry histogram for a given cell type or population and the molecular sequence of the monospecific probe or the target binding region thereof.

As used herein, the term "selection criteria" refers to a series of one or more properties (either quantitative or qualitative) of a monospecific probe which is used as a query to compare the properties of one monospecific probe with those of one or more other monospecific probes.

As used herein, the term "matching information" refers to the properties of a monospecific probe in a database, or the properties of the target of such a probe, that correspond to those of a given set of selection criteria. "Matching information" also refers to that information regarding monospecific probes that is retrieved from a database with a given search query. The term "matching the selection criteria" means that a given monospecific probe has the properties of a given set of search criteria. As used herein, a monospecific probe matching the selection criteria of a given search query does not necessarily exactly meet all qualitative and quantitative aspects of those criteria, but is identified as similar within the parameters of the search technique, algorithm or set of techniques or algorithms used for the comparison.

As used herein, the term "an order determined by each matching monospecific probe's similarity to the selection criteria" means that monospecific probes identified from within a monospecific probe database are ranked with regard to the degree of similarity of each probe identified to the set of search criteria. A probe that is more similar, as determined by the search technique, algorithm or set of techniques or algorithms, will have a higher rank order than one that is less similar by the same search.

As used herein, the term "histogram" refers to a graphical representation or plot of data on a single variable. A histogram according to the invention is a plot of the flourescence intensity of a labeled monospecific probe that binds a target on cells of a population, versus the number of cells having that intensity, for a population of cells. As used herein, the term includes histograms that are raw or unsmoothed and those that have been characterized, for example using kernel smoothing to provide a kernel density estimate yielding a smoothed curve.

As used herein, the term "kernel density estimation" refers to the result of a mathematical process wherein a Gaussian kernel function, K, is applied to a set of i flow cytometry histogram data points using the equation in FIG. 19, wherein $g^i$ is the $i^{th}$ fluorescence intensity channel, h is the bandwidth, and $c^i$ is the number of cells in the population having fluorescence intensity in that channel. Kernel density estimation can have an input of a sample of numbers and an output of a smooth curve representing an estimated probability density function. Alternatively, kernel density estimation can have an input of a coarse histogram and an output of a smooth curve representing an estimated probability density function. For example, when the input is a sample of numbers, if K is the Gaussian kernel function and the sample of numbers is $x_1, x_2, \ldots x_n$, then the estimate at a point x is:

$$f(x)=(1/(nh))*[K((x-x_1)/h)+K((x-x_2)/h+ \ldots +K[(x-x_n)/h]$$

Where h>o is a smoothing parameter known as the band width. Alternatively, when the input is a coarse histogram, if the counts in the histogram are $c_1, c_2, \ldots c_m$ and the centers of the histogram bins are $g_1, g_2, \ldots g_m$, then the estimate at a point x is:

$$f(x)=(1/(nh))*[c_1*K((x-g_1)/h)+c_2*K((x-g_2)/h)+ \ldots +c_m*K((x-g_m/h), \text{ where } h>o.$$

Kernel density estimation provides a fluorescence density function, the derivatives of which define the approximate locations of the peaks and valleys of the histogram by their zero-crossing points.

As used herein, the term "kernel smoothing" refers to the mathematical process of characterizing histogram data wherein a kernel function, K, is applied to a set of flow cytometry histogram data points. Kernel smoothing is a density estimator that results in the reduction of the raw flow cytometry data curve to a curve from which an estimation of the underlying equation a kernel density estimation can be determined.

As used herein, the term "bandwidth" refers to a value for the range of fluorescence intensity x values over which a kernel function is applied in kernel density estimation and kernel smoothing operations. Generally, larger bandwidth values result in a higher degree, or lower resolution of smoothing; conversely, smaller bandwidth values result in a higher resolution or lower degree of smoothing.

As used herein the term "vector space model" refers to the modeling of histograms as vectors in high-dimensional space. Since this modeling is based on histogram features, such as peak and valley location, ascending and descending slopes and histogram dispersion, the vector space is referred to herein as "feature" space. Each histogram's representation in "feature" or "vector" space allows for comparison with features or vectors from other sources. The model is analogous to the standard information retrieval algorithms that permit document ranking, filtering and clustering.

As used herein, the term "relevance feedback" refers to the process whereby a user of a database according to the invention indicates which histogram or histograms of a set of histograms retrieved from the database with a given query is or are most relevant, or most similar to the query. The database then re-calculates the similarity of histograms in the database, giving added weight to the most relevant histogram or histograms identified by the user. This feedback allows the adjustment of histogram similarity groupings that can be important in establishing and maintaining patterns of similarity in a molecular knowledge base.

As used herein, the term "set training" refers to the use of a set of histograms for adjusting the computational comparison of histograms. A training set consists of a set of known matching histograms (i.e., histograms generated by flow cytometry with monospecific probes that bind the same binding target) and a second set of histograms randomly selected from a database of the invention. A training set is used to adjust the comparison of histograms in the database by first combining the two sets and then showing them to a panel of experts in the area of interpreting flow cytometry histograms. The experts judge the histograms pairwise on the likelihood that they are related (deciding that a given unknown is "most likely related" or "unlikely to be related"), and the results are used to adjust the computational comparison of histograms in the database. In other words, the judgements of a panel of experts are factored into the decision of whether a given histogram is similar to another by marking randomly selected database histograms as likely related or not likely to be related to histograms from known monospecific probes. The expert judgements on the relationships of known monospecific probes to the randomly selected monospecific probes in the database establishes similarity relationships between histograms that can not have otherwise been established. These established relationships can then influence the relationships of the known and unknown histograms compared in the training set to other known or unknown histograms in the database.

As used herein, the term "performance measurement" refers to a quantitation of the function of the information retrieval system applied to a database according to the invention. Measurements include but are not limited to: the precision (or specificity) of retrieval of an analytic model, i.e., the number of relevant documents retrieved, divided by the total number of documents retrieved, wherein relevance is judged by the use or independently assessed for relevance by an expert panel; the recall (or sensitivity) of retrieval, i.e., the number of relevant documents retrieved divided by the total number of relevant documents; and/or measurement of the satisfaction of users with the performance of the information retrieval system.

As used herein, the term "comparing" means evaluating the characteristics of one histogram relative to those of another histogram or set of histograms. As used in the invention, comparison can be performed by eye, by computer algorithm, or by a combination of the two. Comparison can be performed on raw histograms or on those that have been subjected to a characterization process such as feature analysis and kernel density estimation.

As used herein, the term "feature analysis" refers to the mathematical modeling or analysis of histogram features, such as peak and valley location, inflection points, ascending and descending slopes and histogram dispersion.

As used herein, the term "similarity of the information relating to a monospecific probe" means the degree to which the information relating to one monospecific probe approaches identity with the information relating to another monospecific probe or set of query data. The degree of information similarity necessary for a mono specific probe to be listed as similar to another depends upon the parameters of the comparison, whether performed manually or by computer algorithm.

As used herein, the term "directory computer" means a computer containing a database of primary data (raw histogram data) and the results of feature analysis. The directory computer will be web accessible and permit queries of the database and return a retrieval result.

As used herein the term "analyzing a histogram by kernel smoothing or kernel density estimation" means subjecting the data generating a histogram to a process involving kernel smoothing or kernel density estimation such that the function(s) describing the histogram data curve is (are) estimated.

BRIEF DESCRIPTION OF THE FIGURES

FIG. 17 illustrates the effect of changes in bandwidth on the degree of smoothing when using kernel density estimators. Panel A shows relatively little smoothing that occurs with a kernel density estimate when a narrow bandwidth is used. Panel B shows the oversmoothing that occurs with a kernel density estimate when a wide bandwidth is used. Panel C shows the kernel density estimate resulting when an intermediate bandwidth is used.

FIG. 18 illustrates the effect of changing bandwidth on the degree of smoothing when using kernel density estimators on a lognormal curve. Panel A shows the effect of a narrow bandwidth, which approximates the mode of the curve well but does not approximate the tail of curve well. Panel B shows the effect of a wide bandwidth, which approximates the tail of the curve well but does not accurately approximate the mode of the curve. Panel C shows the effect of an intermediate bandwidth value, which approximates the mode well while also smoothing the tail of the curve.

FIG. 19 shows the formula for a kernel density estimate of binned data, such as flow cytometry data, where $g^i$ is the $i^{th}$ bin center and $c^i$ is the count of cells in that bin. This formula is referred to herein as "equation (1)".

FIG. 20 shows the first derivative of the kernel function K.

FIG. 21 shows the first derivative of equation (1).

FIG. 22 shows the second derivative of equation (1), in which the inflection points in the histogram curves correspond to the zero-crossing points of the second derivative.

DESCRIPTION

The development of reproducible quantitative flow cytometry provides an opportunity to develop a cumulative molecular database. The flow cytometry histograms produced using a reproducible quantitative flow cytometry method are reproducible over time, such that any given histogram in the database can be compared with any other histogram in the database regardless of when the data and the histograms were generated. The validity of comparing histograms over time means that the histogram repository is more than just a database, and can actually serve as a molecular knowledge base that can be analyzed to identify previously unknown patterns or relationships between members of the database.

The reproducibility of the quantitative flow cytometry data is critical to the practice of the invention. In order to maintain the reproducibility and reliability of the data, which will necessarily be obtained in different flow cytometry runs and will be obtained over times that can possibly encompass years, the flow cytometry data useful in the invention are collected in a limited number of laboratories, herein termed "reference" laboratories. It is preferred that a single reference laboratory is established to collect quantitative flow cytometry data for use in the invention, although two or more reference laboratories can also be established if sufficient quality control measures are taken as described herein below. It is preferred, although not absolutely necessary, that all quantitative flow cytometry data be collected on a single high resolution flow cytometer. This will minimize the possibilities for variation in the data.

According to the Invention:

1) A reference laboratory is established that performs quantitative flow cytometry on mono specific probes submitted by participating investigators.

2) Quantitative flow cytometry histograms produced by the reference laboratory are characterized using mathematical techniques including feature analysis and kernel density estimation.

3) An information retrieval system composed of intelligent search agents and knowledge discovery tools facilitates "best match" histogram retrievals.

4) Electronic communication (the internet or the world wide web) is used to make the knowledge base available to investigators around the world, facilitate the day-to-day work of participating investigators, and facilitate relevance testing of the knowledge base.

Figure 1:
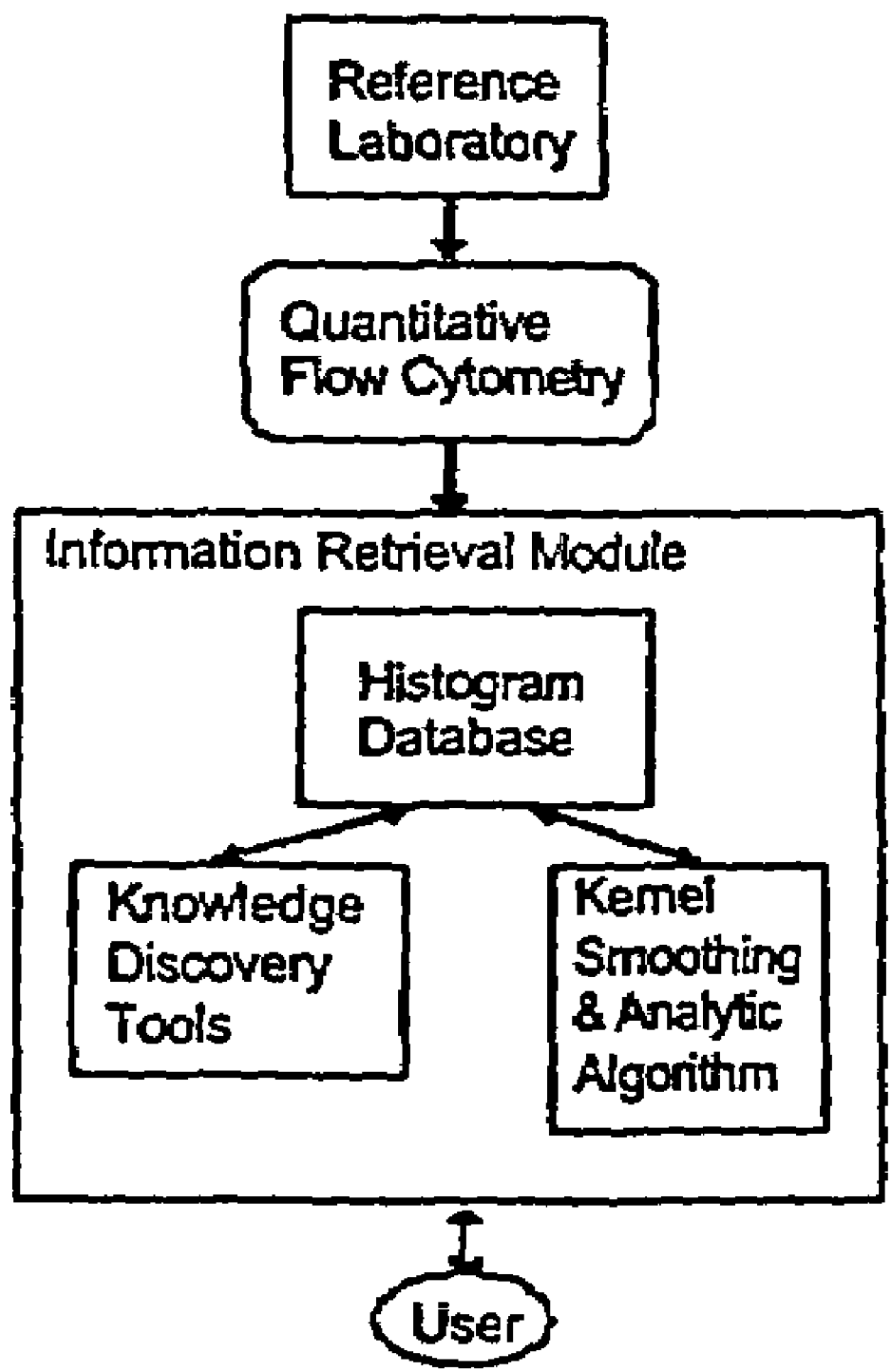
FIG. 1 shows a schematic diagram of the general architecture of the invention.

An overview of the architecture of the invention is shown schematically in FIG. 1. The rapid development of Web-centric technologies will permit the knowledge base of the invention to be available to investigators around the world 24 hours a day. The monospecific probes submitted to the reference laboratory can be processed and the data immediately posted on the Web. The real-time characterization of new monospecific probes will shorten the development time of new probes, facilitate their utilization in ongoing research, and encourage the development of more probe molecules.

Additionally, it is hoped that the rapid accessibility of new data in the knowledge base, as well as its around-the-clock availability, will encourage investigators to frequently "log in" to the database. The intellectual participation of investigators in discussion threads, and consequently their enhanced familiarity with recent molecular developments, can hasten the pace of research as well as encourage international and cross-disciplinary collaborations.

The invention also provides a data set that can be used to refine the existing analytic algorithms using a "manageable" database. The refinement of these algorithms will enable computer searches for relationships between known and unknown monospecific probes.

Single Reference Laboratory

The reliance of the knowledge base on quantitative flow cytometry assumes the rigorous application of stringent techniques and quality control procedures. Based upon experience in a five year pilot study, the greatest variability was due to the nonlinear gain in some flow cytometers, which is particularly observed at high cell surface densities. These machines were occasionally sensitive to "warm-up" time and other less predictable electronic variables.

Figure 2:
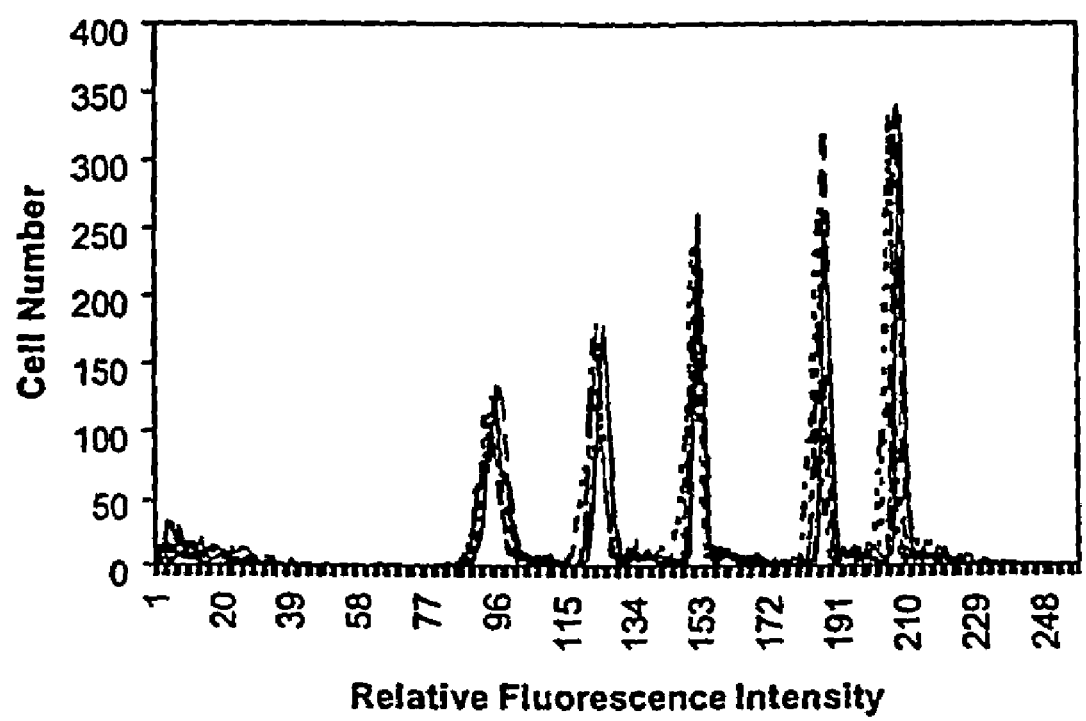
FIG. 2 shows a flow cytometry histogram with the superimposition of five randomly selected calibration curves created over the five year span of a pilot study.

The requirements for reproducible (i.e., standardized) flow cytometry are best met by a single reference laboratory, and preferably a single flow cytometer. There are a number of approaches to insure reproducibility and reliability of the data, even within a single reference laboratory. For example, the flow cytometer should use digital signal processing to minimize amplification error. In addition, the meticulous development of reagent and procedural quality control measures are best instituted at a single laboratory. Further, calibration distributions using standards with known markers in known concentrations are performed on a regular basis, including, but not limited to, before each flow cytometry run with an unknown monospecific probe. Also, each flow cytometry run includes both negative and positive internal control probes. Details and examples of procedures and controls designed to standardize the histograms resulting from the flow cytometry are presented below. The reproducibility of the single laboratory approach is demonstrated in the calibration distributions that were selected at random from calibrations performed over a span of five years (see FIG. 2).

Process Applied to Samples Submitted to the Reference Laboratory

Figure 3:
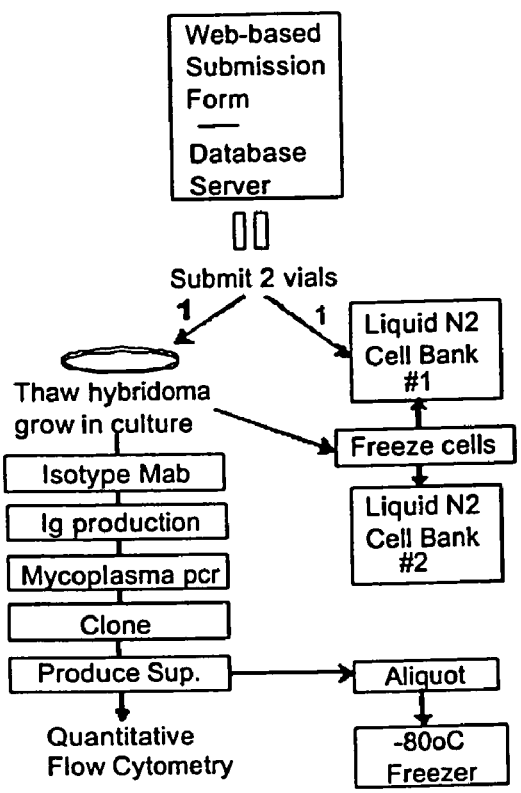
FIG. 3 shows a schematic diagram of the processes performed by a reference laboratory according to the invention.

The process that is applied to each monospecific probe submitted to the database of the invention is described in the flow diagram of FIG. 3. The first set of steps is designed establish stocks of monospecific probe and to broadly characterize the monospecific probe with regard to concentration, purity, and isotype (e.g., for probes that are monoclonal antibodies). Following this initial characterization and the establishment of secure stocks of the monospecific probe, quantitative flow cytometry is conducted using the new monospecific probe in order to generate histograms for inclusion in the database of the invention. A panel of different cell types is evaluated with each new monospecific probe in order to determine the expression pattern of the target or binding moiety recognized by that probe on cells of the panel. The resulting histograms that are then processed or analyzed using computational processes designed to allow subsequent computer comparison of the histograms while retaining critical information within them.

A. Initial Characterization

The following describes the steps involved in the initial characterization of monospecific probes submitted for inclusion in the database of the invention. The steps are described as they would be applied to a monoclonal antibody but can be generalized to apply to any type of monospecific probe, such aptamers, peptides, lectins, etc.

1. The isotype of the antibody secreted by a hybridoma is characterized by flow cytometry. The cells used for isotyping of the monoclonal antibodies will be those known to express relatively high levels of the target molecule (as reported on the submission form). Isotyping is a useful initial procedure to establish an estimate of monoclonality (P4).

2. The concentration of monoclonal antibody in the supernatant is assessed. The cell lines must produce sufficient antibody to permit the use of monoclonal antibody-containing supernatants; ascites will not be produced. The goal is to eventually establish production thresholds similar those establish for hybridoma cloning (P5).

3. The cell line is screened for Mycoplasma contamination using PCR. Mycoplasma detection by PCR is performed using methods known in the art. The procedure can be efficiently carried out using any of a number of commercially available screening kits that generally contain primers annealing to conserved regions of the mycoplasma genome. PCR detection kits are available, for example, from Stratagene, Panvera, and ATCC. Primer sets in these commercial kits can produce either a single band as a plus-minus indicator of mycoplasma infection or multiple product banding patterns that must be interpreted to confirm the presence of mycoplasma. As an example, the Mycoplasma Plus™ PCR Primer Set from Stratagene amplifies a single 874 bp product if mycoplasmal DNA is present in an extract from the cultured cells. Mycoplasma positive cell lines will not be studied or included in the database of the invention.

4. Hybridoma cell lines are re-cloned to limit overgrowth by irrelevant or non-producing hybridoma cells. The problem of hybridoma population dynamics has been addressed by a technique that permits frequent cloning of hybridomas in a reversible three-dimensional alginate matrix (described in Li et al., 1992, Hybridoma 11: 645–652). The hybridoma cloning can be performed without a feeder layer and with a minimal amount of serum-containing medium. The three-dimensional matrix also permits simultaneous screening for monoclonal antibody production.

5. Aliquots of the supernatant are stored in a −80° C. freezer to insure longitudinal reproducibility as well as provide a comparison for future supernatant production.

At the conclusion of the processing of the monospecific probe, the data are confidentially shared with the contributing investigator. A mutual decision is made regarding the inclusion of the probe in the database. Hybridomas that are Mycoplasma contaminated, insufficiently productive or not monoclonal will not be included in the database.

B. Quantitative Flow Cytometry

Figure 4:
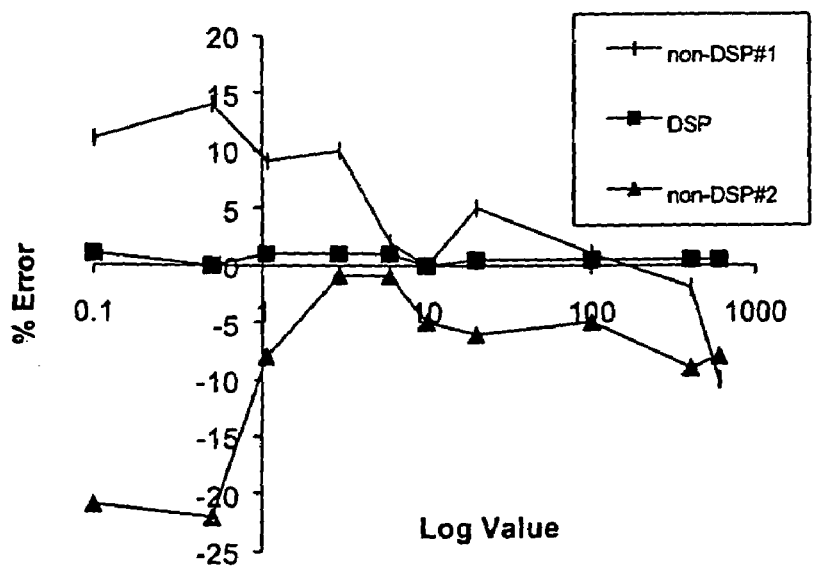
FIG. 4 shows a graph comparing the percent error of three different flow cytometers, one with (squares) and two without (triangles and bars) digital signal processing (DSP).

The most important aspect of quantitative flow cytometry is stringent quality control and calibration procedures. In pilot studies, the greatest variability was derived from electronic variables such as log amplifiers and instrument-to-instrument variability. To address this issue, it is preferred that a flow cytometer with digital log transformation (e.g., Epics XL) be used. Digital signal processing (DSP) substantially improves log scale linearity and the reproducibility of the calibration procedure when compared to other analyzers (non-DSP). The data in the following graph are courtesy of Beckman-Coulter Corporation, and compare the % Error of flow cytometers with and without digital signal processing (see FIG. 4).

1. Calibration Methods

The flow cytometry experiments are calibrated using Sphero Rainbow Calibration Particles (SpheroTech, Libertyville, Ill.). Calibration profiles are generated before each flow cytometry run analyzing a newly submitted probe. Because of the variation in cell size and the need to maximize information content of the histograms, three distinct calibration curves are used. These three calibration curves correspond to the calibration of the flow cytometer for small cells (e.g. thymocytes and lymphocytes), medium-sized cells (e.g. macrophages), and large cells (e.g. endothelial cells). The three calibration curves are designed to maximize the resolution of the single parameter histogram. Calibration particles are used as a reference for calibrating the flow cytometer into the three windows: small cells, medium-size cells and large cells. The machine calibration is designed to ensure that the entire distribution of the negative control and brightest positive control are included in the recorded data.

2. Reference Panel

To ensure reproducible cell populations, a panel of known monospecific probes is included in all flow cytometry experiments. These "reference panel" monospecific probes are specific to each cell population studied. The monospecific probes in the reference panel will characterize the cell population as well as provide an internal experimental control. These monospecific probes will also provide a measure of replicate variability in the database.

Figure 5:
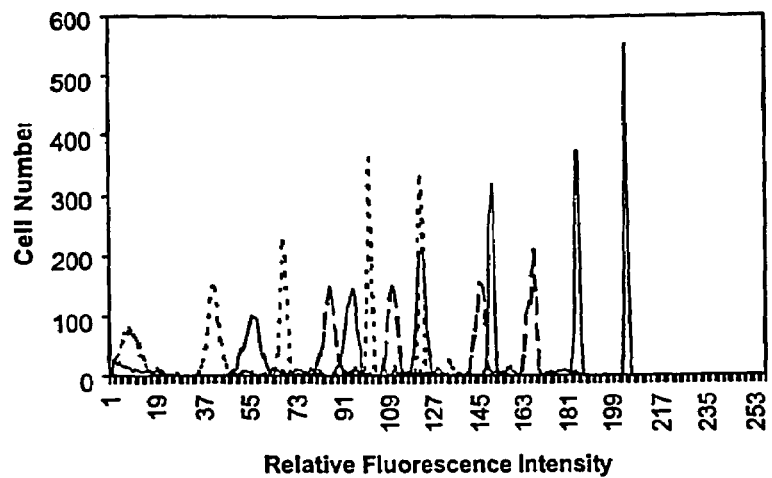
FIG. 5 shows a histogram with the results of three different size calibration flow cytometry runs.

Each flow cytometry series using any given monospecific probe and any individual cell type or population includes negative and positive control probes selected for the absence and presence, respectively, of binding moiety expression in that cell type. An example of a negative control is the use of a fluorescein-conjugated secondary (or detection) antibody without a primary antibody. The detectable fluorescence on the cells would be due to nonspecific binding of the detection antibody. For all the cells tested, the negative control distributions are included in their entirety at the far left of the distribution. In addition to the data points representing the fluorescence signals of the negative control probes, each histogram includes, at the far right and in their entirety, the distribution of high-density molecules, such as MHC class I molecules (see FIG. 5). Within any given cell type and with any given monospecific probe, these internal control distributions are expected to remain essentially constant regardless of the probe type or binding moiety abundance for a given monospecific test probe.

Directly-labeled monospecific probes will be used to define subpopulations in select two-color flow cytometry experiments. In our experience, reliable calibration is only possible in one dimension. Dual parameter flow cytometry can be done with carefully selected monospecific probes. For example, two color analysis can be performed on discrete populations such as CD4+ and/or CD8+ lymphocytes. In the studies, the second and third parameters of analysis are used for gating purposes, not for the acquisition of quantitative historgrams. Using these approaches, the reference laboratory can produce reliable flow cytometry histograms for inclusion in the molecular database.

C. Other Information Useful in Characterizing Monospecific Probes

Figure 6:
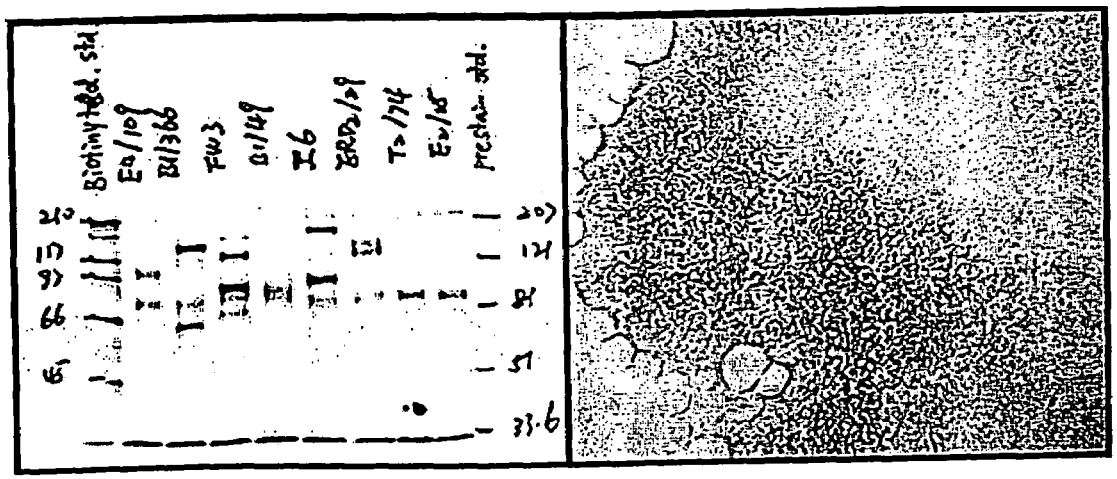
FIG. 6 shows an example of experimental monospecific probe data that are generated in addition to flow cytometry data by a reference laboratory and made available on the web site with histogram data. The panel on the left shows an immunoblot of proteins from various tissues and a digital photomicrograph of immunohistochemistry of the thymic cortex.

Additional information is frequently useful in confirming the identity of the binding target of a given monospecific probe. In a pilot study, the most useful ancillary studies were 1) molecular weight determined by immunoblotting (P2), and 2) tissue immunohistochemistry. Previous work focused on small format immunoblotting (P2). It is clear from this experience that the reference laboratory should use a large format immunoblot system. The subtle banding differences in the 130 kD to 200 kD range, regardless of the gel gradient used, will require a large format for adequate electrophoretic resolution. The typical approach develops the bands on photographic film using enhanced chemiluminescence. The developed photographic film is then scanned and made available on the web. For tissue immunohistochemistry, we perform typical ABC immunohistochemistry is performed on a so-called "six organ" tissue section. These microscope slides are prepared with samples of aorta, lymph node, thymus, spleen, Peyer's patch and lung. The following illustration is an immunoblot and digital photomicrograph (immunohistochemistry of thymic cortex; BW of RGB micrograph) that has been previously posted on our web site for discussion and comment (see FIG. 6). These confirmatory studies would be generally performed once the identity of the target molecule has been nearly established by flow cytometry.

According to the invention, monospecific probes are used in flow cytometry assays of a panel of different cell types. Useful cell populations include cell lines, when available, as well as naturally occurring cell populations. Non-limiting examples of naturally-occurring cell populations include the cells in the peripheral blood, lymph nodes, spleen, thymus gland, and alveolar macrophages.

D. Characterization of Flow Cytometry Data

The invention relies upon the characterization of flow cytometry data, a process that permits the comparison of such data over a broad spectrum of cell types and conditions. The comparison permits the creation of a molecular database for monospecific probes specific for targets in any animal, including but not limited to human and large or small mammals. An example of a large mammal is a sheep.

The invention provides a database of single parameter histograms produced by monospecific probe staining of a variety of cell types assessed by quantitative flow cytometry. When the characterization of flow cytometry data is applied across multiple cell types and subpopulations, the histograms become a "molecular fingerprint" for the target of a given monospecific probe. The database becomes a "knowledge base" with the validation of its knowledge discovery tools and demonstration of its cumulative value as a scientific resource. Techniques useful according to the invention for the characterization of flow cytometry data are described below.

1. The Complexity of Histogram-Matching

One purpose of the database of the invention is to provide a database of monospecific probe histograms that can be compared in order to aid in the determination of the binding targets of unknown probes. In the absence of a database enabling computer analysis techniques, investigators make comparisons of flow cytometry histograms essentially by eye on a pairwise basis. The major challenge of histogram analysis is "scaling-up" the technique of simple inspection of a small number of histograms to the computerized analysis of a database consisting of thousands of histograms. The subtle relationships between histograms are lost by conventional mathematical characterizations of the histograms. For example, the "percent positive" cells, the mode of the histogram distribution, or the calculated density of the cell surface molecule are commonly used representations. These characterizations, while simplifying the data, do not preserve the structure of multimodal single parameter histograms. Thus, in the absence of the database of the invention, the utility of quantitative flow cytometry is lost when the molecular database consists of too many histograms to characterize by visual inspection.

Figure 7:
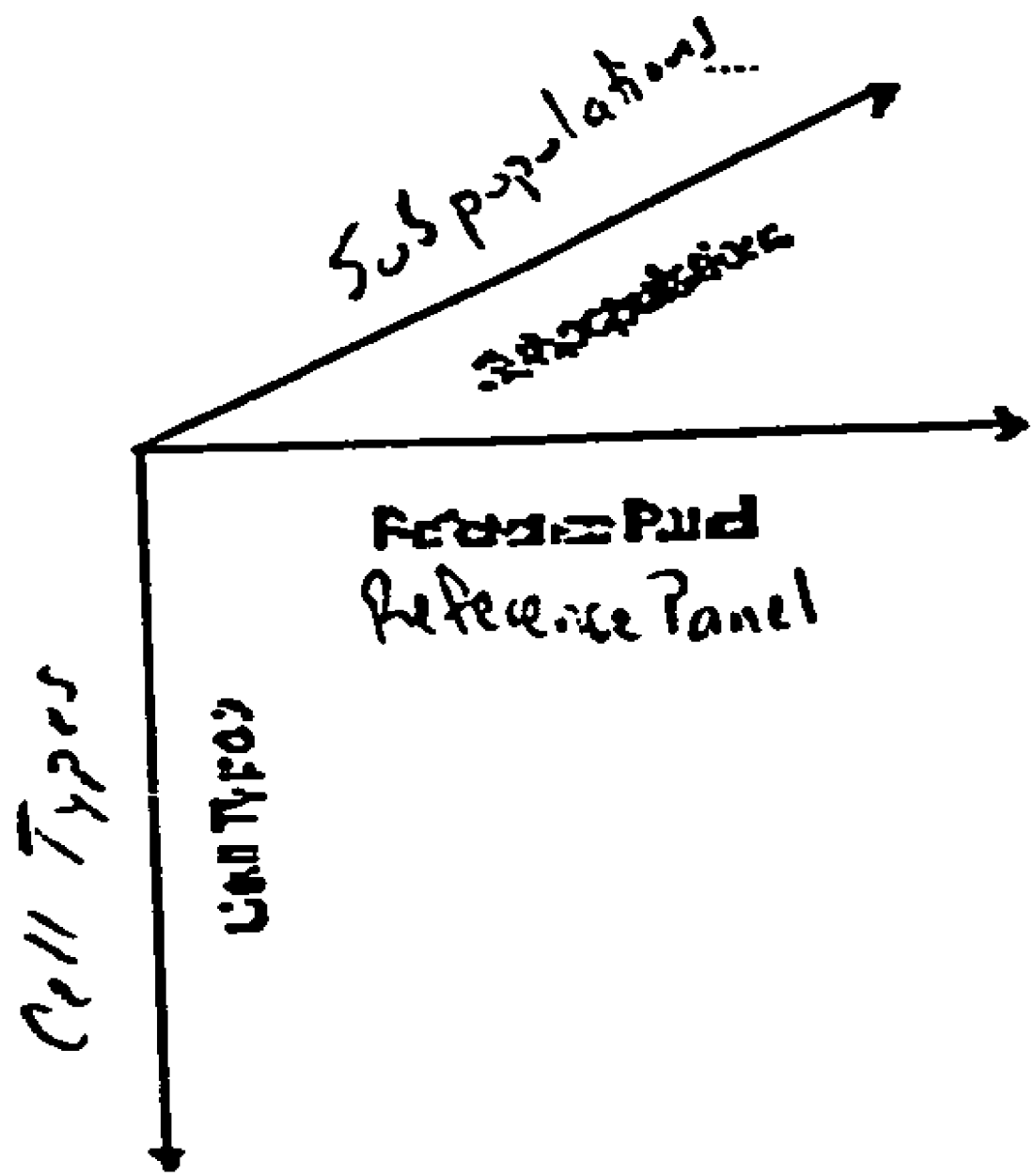
FIG. 7 shows a schematic of the three-dimensional database "matrix" containing information generated for each monospecific probe submitted tot he database. Information is collected regarding the binding of monospecific probes to different cell types and subpopulations within them, and compared with the binding of a "reference panel" of monospecific probes to the same cell types and/or sub-populations.

The histogram database can be conceptualized along several dimensions. For any given cell type, a monospecific probe will produce a histogram that will be compared to a "panel" of monospecific probes. The "panel" will consist of the monospecific probes actually tested on the same day using the same experimental procedure. The "panel" histograms are used for internal comparisons that validate the cell populations and the technical performance of the individual experiment. These histograms also contribute to the cumulative database. The "unknown" monospecific probe histograms are compared to the "panel" histograms as well as to the histograms archived in the database. This process is repeated on many different cell types and subpopulations within the cell types. The result is a three-dimensional database "matrix" for each monospecific probe (see FIG. 7).

Figure 8:
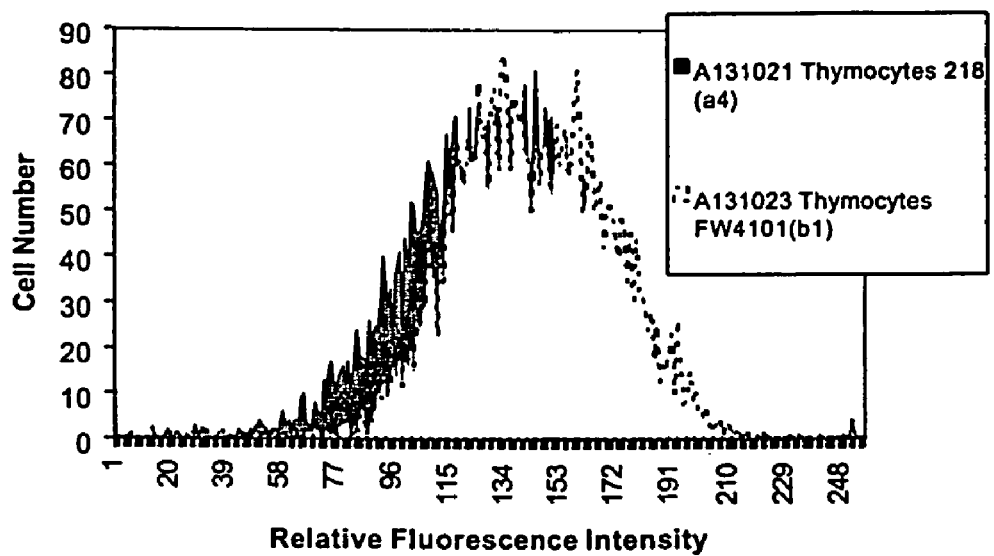
FIG. 8 shows the direct comparison of the flow cytometry histograms generated with two different monoclonal antibodies that recognize related molecules, VLA-4 and β1 integrin.
Figure 9:
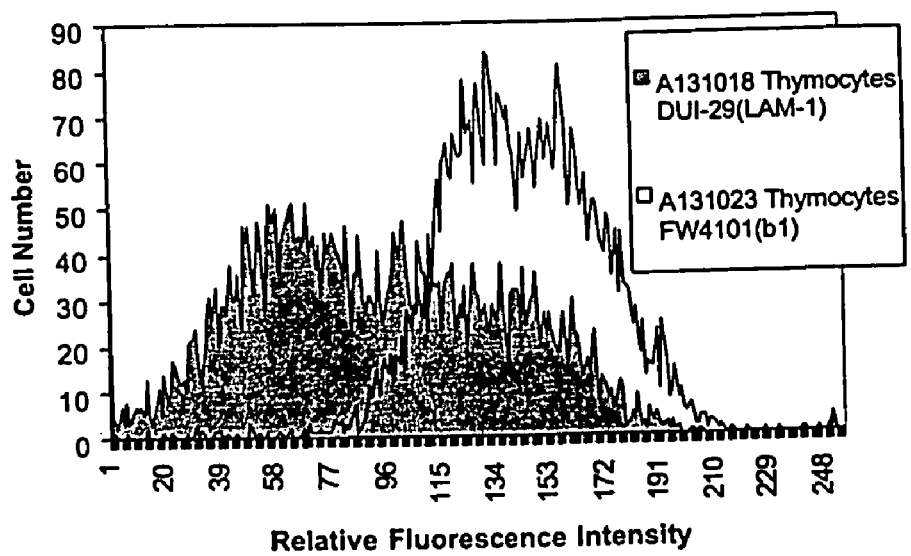
FIG. 9 shows the direct comparison of flow cytometry histograms generated with two different monoclonal antibodies that recognize unrelated molecules, LAM-1 and β1 integrin.

In most laboratories, the comparison between monospecific probes is based on the similarity of single parameter flow cytometry histograms. Simple inspection is largely based on the "overlap" of the flow cytometry histograms. For example, the distribution of the 10,000 of events in the beta-1 integrin (b1, below) histogram is directly compared to the distribution of the same number of events of the VLA-4 (a4, below) histogram. Since these two molecules are related, one might expect substantial overlap. This molecular relationship is supported by quantifying the area of overlap: 7560 events are shared; only 2440 events are nonoverlapping (see FIG. 8), gray areas). In contrast, L-selectin (LAM-1, below) and beta-1 integrin (b1, below) are unrelated molecules. The lack of a molecular relationship is obvious by simple inspection of the histograms. These two molecules share less than 4550 of the events in their histograms (see FIG. 9).

In its simplest form, histogram-matching weights each event equally. The fluorescent event (cell fluorescence) is weighted the same whether it is negative or positive, and its importance is independent of the distribution as a whole. This democratic approach clearly does not reflect the complexity of biologic systems, nor does it reflect the cognitive weighting intuitively performed by experienced investigators when visually inspecting histograms. When examined by an experienced investigator, the histograms are typically compared for subtle differences. In a pilot study, five situations in which simple histogram "overlap" does not accurately reflect biologically important comparisons were identified. An important design feature of the database is to develop analytic techniques that can recover the qualitative features of these histograms.

a. Subpopulation Weighting: Good Things in Small Peaks

Figure 10:
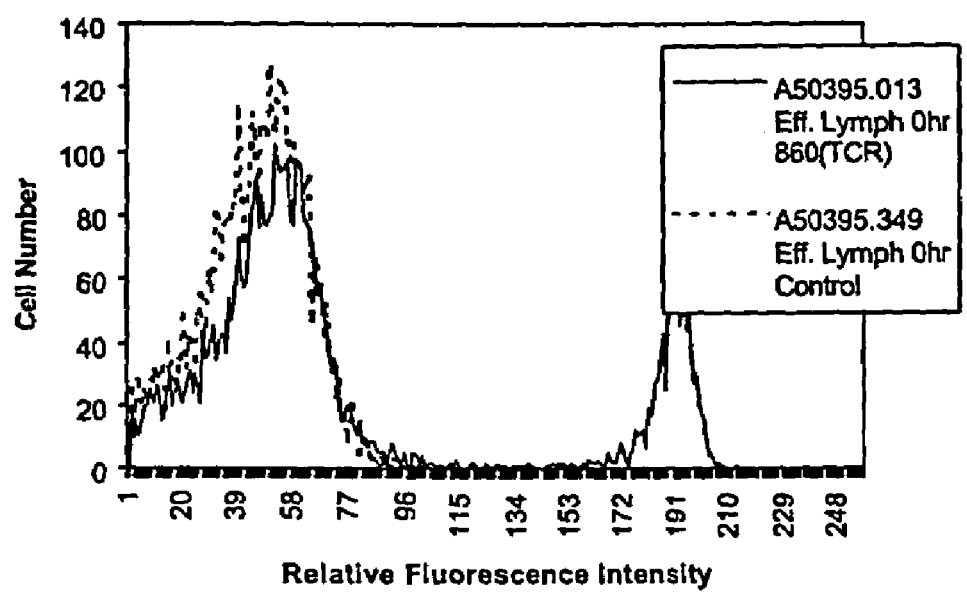
FIG. 10 shows the direct comparison of flow cytometry histograms wherein a monospecific probe (a monoclonal antibody for a T cell receptor variable region) recognizes a small sub-population (broken line) of the whole population recognized by another monospecific probe (solid line).

In some cases, the differences can be small subpopulations that are distinct from the dominant "negative" distribution. For example, monoclonal antibodies that recognize T-cell receptor variable regions can bind to only 3 to 5 percent of the cells in the distribution. These events will have high relative fluorescence intensity, and be distinct from the negative cells in the distribution. In the following distribution, the numerical "overlap" of the negative control and the TCR monoclonal antibody is identical (7500 events) to the related molecule shown earlier (b1 integrin and VLA-4). The shapes of the histograms, however, are quite different (see FIG. 10). An analytic approach useful for purposes of a knowledge base would need to be able to describe the qualitative features of these small populations.

b. Mediator Induction: Small but Diagnostic Change

Figure 11:
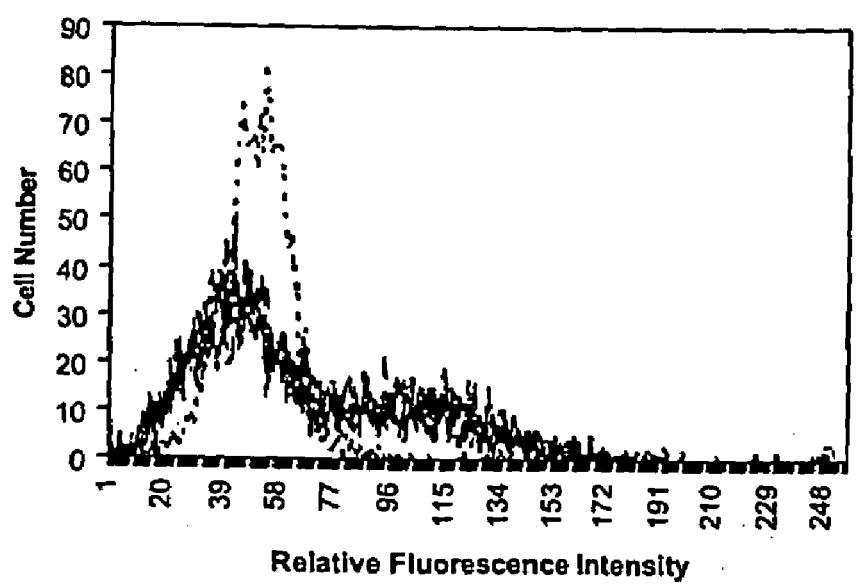
FIG. 11 shows the direct comparison of flow cytometry histograms generated using a monospecific probe for VCAM-1 on populations of either unstimulated (solid line) or IL-1-stimulated endothelial cells (broken line).

In other cases, the difference can be a small shift in the dominant distribution from "negative" to "positive." For example, the molecule can be selectively induced by cytokines or perhaps the surface expression is dependent on the cell cycle. Because these behaviors are unusual relative to most membrane molecules, they provide distinguishing data that can be useful in identifying the target molecule. For example, ICAM-1 is a molecule with a broad molecular weight band by immunoprecipitation (70–90 kD), nonspecific tissue staining characteristics, and relatively weak in vitro functional activity. The most distinguishing feature of the ICAM-1 molecule is the induction of its expression by IL-1 on endothelial cells. Any monoclonal antibody that might recognize ICAM-1 would necessarily have to demonstrate increased binding to endothelial cells after IL-1 induction. Similarly, VCAM-1 is a membrane molecule whose expression is selectively induced on endothelial cells. VCAM-1 is not expressed on resting endothelial cells as shown below. In contrast, VCAM-1 can be induced by IL-1. The reproducibility of the expression is documented by four different VCAM monoclonal antibodies (see FIG. 11).

In all of these cases, the difference in the overlap is relatively small, but diagnostic of the target molecule's identity. The database "descriptors" used to characterize these histograms would need to be sufficiently sensitive to reflect these small changes.

c. Contour Weighting: Quantifying a Histogram Gestalt

In contrast to small differences in histograms that can reflect important biologic differences, relatively large differences in histogram overlap can still reflect important molecular similarity. In the following histogram, the contour of both curves is strikingly similar. The overlap, however, is only 7500 events (see FIG. 12). In this example, the overlap is only modest, but the molecular relationship is strongly implied. The analytic techniques used in the knowledge base would need to reflect the qualitative features, or the peaks and valleys, of these histograms.

d. Molecular Families: the Exception Proves the Relationship

Important information is revealed not only by individual histograms, but by the "pattern" of histograms across several different cell types and subpopulations. Monospecific probes recognizing structurally or functionally related molecules frequently demonstrate remarkably similar histograms on many cell types. In most cases, however, the histograms will diverge on at least one cell type. If all the histogram data were combined in an unweighted algorithm, the important difference might be lost. These potential pitfalls are apparent when considering molecular relationships in the context of multiple subunits. For example, the LFA-1 molecule is composed of an a (CD11a) and a b (b2 integrin) subunit. Because the LFA-1 molecule is the only b2 integrin expressed on lymphocytes, monoclonal antibodies recognizing the a and b subunits will have identical cell labeling patterns. In contrast, granulocytes and monocytes express 3 different alpha subunits (CD11a, CD11b, and CD11c) associated with the b2 integrin subunit. The same monoclonal antibody recognizing CD11a will have a very different histogram from the antibody recognizing b subunit when tested on granulocytes or monocytes. If the histogram comparison was compiled across cell types, the identical staining of these two monoclonal antibodies on lymphocytes would be lost. The molecular relationship clearly implied by the identical staining on lymphocytes would be "washed out" by the discordant staining on granulocytes and monocytes.

Figures 12, 13:
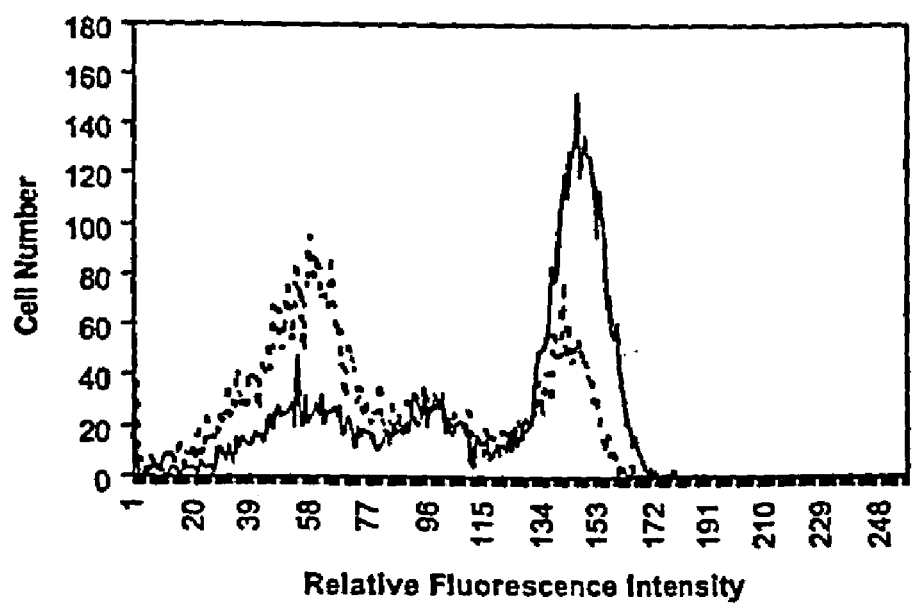
FIG. 12 shows the direct comparison of flow cytometry histograms in which the absolute degree of overlap is not very large, but where the pattern of expression or binding is similar, thereby implying a possible relationship between the targets.
FIG. 13 shows a table describing the pattern of histograms for structurally or functionally related targets that are expressed in different patterns on different cell types.

A hypothetical illustration of this problem is shown in the table of FIG. 13). There are two monospecific probes: one of the monospecific probes recognizes the a1 subunit and the other recognizes the b1 subunit. The two monospecific probes have identical expression on several cell types. These two monospecific probes, however, have strikingly discordant expression on another cell type. Without a sophisticated retrieval system, this related pattern of reactivity is obvious only in retrospect.

e. Technical Variance: Nobody is Perfect

Finally, there will be histogram variability due to technical reasons. For example, monoclonal antibodies that recognize the same target molecule can have differences in antibody affinity. Differences in antibody affinity can theoretically produce different flow cytometry histograms. Because of the methods typically used to screen monoclonal antibodies, most monoclonal antibodies have comparable affinity. More likely is the possibility that monoclonal antibodies will produce different histograms because of differences in isotype. It is possible that investigators can find systematic differences in histogram profiles when comparing IgG and IgM monoclonal antibodies. The knowledge base and information retrieval system must be sufficiently robust to account for this type of variability.

2. Approaches to Histogram Comparison

Several approaches to histogram comparison and their applicability according to the invention are described below.

a. Parametric Approaches

The data set obtained from quantitative flow cytometry usually involves 1-dimensional frequency distributions, or histograms, of cellular fluorescence. The histogram composed of 256 or 1024 channels is the standard graphical display of flow cytometry data. The histograms are stored as list mode data in Flow Cytometry Standard (FCS 2.0) computer files. In many early flow cytometry applications, the data set was derived from in vitro cell lines. Because cell lines are typically homogeneous in the expression of membrane molecules, the flow cytometry histograms can produce a parametric distribution such as a normal, or Gaussian, distribution. Other molecules can produce binomial or Poisson distributions. The ability to describe some histograms using parameters of these models led to the use of a variety of parametric tests including measures of central tendency and measures of dispersion. There are, however, statistical drawbacks to parametric modeling. The primary limitation of parametric modeling in flow cytometry is that the models are too restrictive and rigid. The danger is that the application of these models will lead to incorrect conclusions. Most flow cytometry histograms deviate substantially from normal. When parametric approaches are applied to flow cytometry histograms, they produce models with large bias and consequently with low modeling and predictive capability. In the context of a histogram knowledge base, the cost of statistical inaccuracies grows as the size of the database increases.

In the past few years, software applications have developed advanced graphical capability, but few new analytic tools. The analysis of the graphical display has typically involved histogram "subtraction" or Kolmogorov-Smirnov (KS) statistics. Histogram subtraction is the simplistic approach that defines the degree of "overlap" between histograms. This approach can provide one estimate of the similarity between two histograms, but can fail to appreciate more complex relationships (see, for example, sections 1–5 above). Similarly, cumulative distribution functions such as Kolmogorov-Smirnov do not provide sufficient resolution to describe a "molecular fingerprint" or provide meaningful longitudinal data. This is not to say that parametric approaches to histogram comparison are never of use according to the invention. Under some circumstances it is possible that a characterization based on a parametric approach can be sufficient to describe the flow cytometry data in a manner allowing the comparison of data from different probes without obscuring essential characteristics of the data. Generally, the simpler the histogram profile, the more readily it can be characterized using parametric approaches. For example, data generating a histogram with a unimodal profile will be more readily compared with parametric characterizations than will those with bimodal or multimodal profiles.

b. Non-Parametric Approaches

The challenge for scaling up the process of histogram comparison is the development of analytic approaches that can be used with more complex cell populations and "multimodal" histograms that are not accurately characterized with parametric approaches. Several nonparametric smoothing methods exist for fitting curves produced by observational data. These include, for example, approaches using spline functions and kernel smoothing. Some of these computational approaches are available on Matt Wand's "Home Page" (http://biosun1.harvard.edu/). It has not previously been appreciated that non-parametric histogram characterizations would be useful for the comparison of flow cytometry data.

Spline Functions

When approximating functions for complex data sets, such as those generated by flow cytometry, it is necessary to have classes of functions which have enough flexibility to adapt to the given data, and which, at the same time, can be easily evaluated on a computer. Polynomials are often used to describe complex data curves. However, for rapidly changing values of the function to be approximated, the degree of the polynomial has to be increased, and functions exhibiting dramatic oscillations can result. An approach that addresses this problem is to divide the interval into sub-intervals, and approximate the function for each sub-interval such that the function is represented by a different polynomial over each subinterval. The polynomials are joined together at the interval endpoints (knots) in such a way that a certain degree of smoothness (differentiability) of the resulting function is guaranteed. If the degree of the polynomials is k, and the number of subintervals is n+1 the resulting function is a (polynomial) spline function of degree k (order k+1) with n knots.

Spline functions are smooth and flexible, readily amenable to computer manipulation and storage, relatively easy to evaluate, and can be generalized to higher dimensions. Spline functions are described by Press et al. (W. H. Press, S. A. Teukolsky, W. T. Vetterling, and B. P. Flannery, Numerical Recipes in C, Second edition, Cambridge University Press, 1995), Flowers (B. H. Flowers, An Introduction to Numerical Methods in C++, Oxford University Press, Oxford, 1995), and by de Boor (C. de Boor, A Practical Guide to Splines, Springer, Berlin, Heidelberg, 1978).

Kernel Density Estimation and Kernel Smoothing

Figure 14:
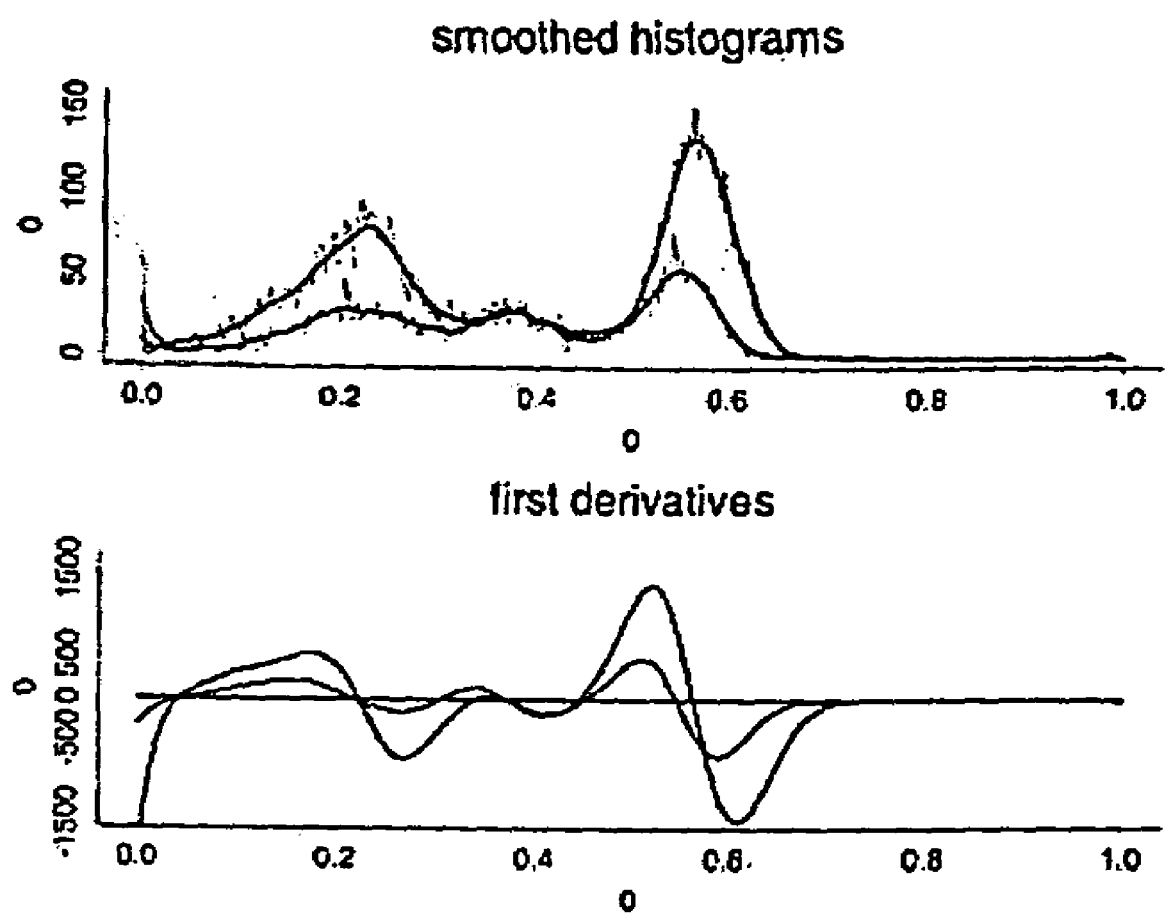
FIG. 14 shows an example of the application of kernel smoothing to two histogram data curves for two different monospecific probes (top panel), and a plot of the first derivatives of the smoothed histograms showing coincident peaks and valleys in the data that imply a relationship between the targets of the monospecific probes.

Kernel density estimation is a more sophisticated alternative to the histogram for the recovery of structure in data sets. Kernel smoothing, has the advantage over other techniques in being very intuitive and relatively straightforward to analyze mathematically. Kernel smoothing is a general-purpose statistical technique for highlighting structure in nonparametric data sets. A simple example of kernel smoothing is the five-day moving average of daily maximum temperatures for Boston. Another practical example of the application of kernel smoothing is the 200 day moving average of the stock market. There now exist many sophistications of this basic notion (Wand and Jones, 1995 (P8)). A recent development is the design of kernel estimators that can be incorporated into a database. A simple example of kernel smoothing is shown graphically below (see FIG. 14). In order to place data into a form that can be readily compared, the histogram is first smoothed and then derived from the underlying density function. Note that the derivatives of the first two peaks reflect their intuitive similarity with coincident zero crossings.

Figures 15, 16:
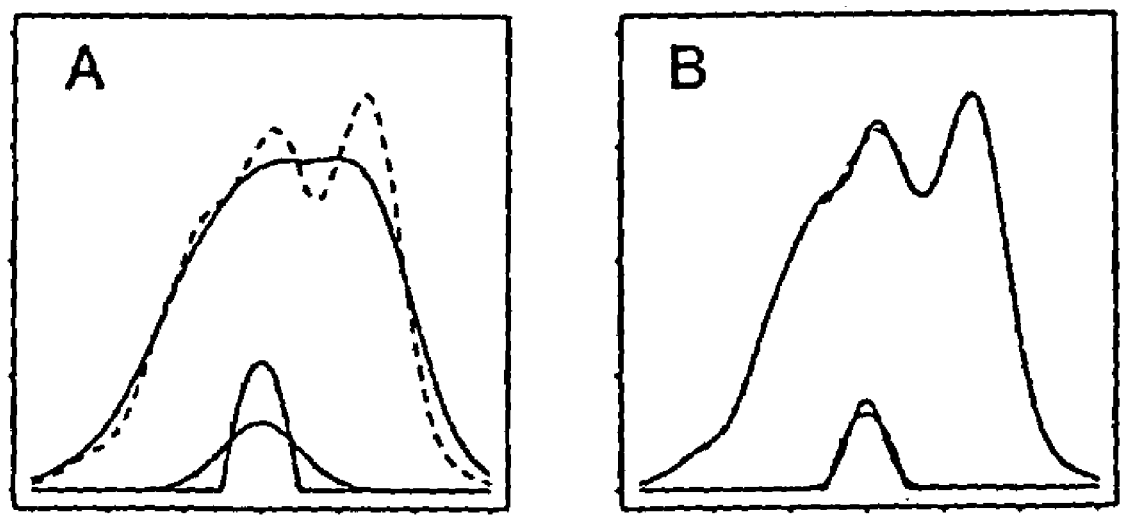
FIG. 15 shows the general formula for a kernel density estimate at an arbitrary location x.
FIG. 16 shows two kernel density estimates of the same histogram using the same bandwidth and different kernels. Panels A and B illustrate the effects of different kernel masses on peak resolution (bandwidth is constant between panels).

The process of kernel smoothing, mathematical derivation and the application of these to the comparison of sets of measurements on a single variable (e.g., flow cytometry histograms) is described below. If $x1, \ldots, x_n$ represents n measurements on a single variable (e.g., fluorescence intensity), then the kernel density estimate at an arbitrary location x is given by the equation in FIG. 15), where K is a symmetric function that integrates to unity, known as the kernel function, and h is a positive number called the bandwith. Although bandwidth plays the dominant role in kernel smoothing, the shape of the kernel function is relevant. A special subset of kernels, called canonical kernels, are useful for the illustrative comparison of density estimates. Canonical kernels are defined in such a way that a particular single choice of bandwidth gives roughly the same amount of smoothing. In the following example (adapted from Wand and Jones, 1995 (P8)), kernel density estimates are based on equal bandwidth and different kernels. In panel (B) of FIG. 16), the canonical kernel gives estimates that are almost identical (the small curves at the base of the graph represent the kernel mass for each estimate).

Despite this particular illustration, the choice of the shape of the kernel function is generally not important. The choice of the value for the bandwidth, however, is very important. The value of h has a profound influence on the appearance of the resultant curve. If h is chosen to be very small, then the kernel density estimate will tend to mimic the measurements themselves (i.e. a small amount of summarization). The narrowness of the kernel means that the averaging process performed at each point is based on relatively few observations. This results in a very rough estimate that does not allow for variation across samples. The result is said to be undersmoothed (FIG. 17, panel A). If h is very large, then the kernel density will be a single hump encompassing the data. The result is really too smooth since the bimodal structure has been smoothed away and the curve has no localized features apparent. This is an example of an estimate that is oversmoothed (FIG. 17, panel B). Intermediate values of h that highlight the features of the histogram are usually the most useful. As is illustrated in FIG. 17, panel C, a compromise in bandwidth can be reached. In this illustration, the kernel estimate is not too noisy, yet the essential structure of the underlying density has been recovered (adapted from Wand and Jones, 1995 (P8); the kernel weight for each estimate is illustrated by small kernels at the base of the figures).

Another illustration below shows the importance of bandwidth. This illustration also shows a potential difficulty with the kernel density estimator. The limitation of the kernel estimators is that just a single smoothing parameter is used over the entire histogram. Despite this limitation, even difficult curves such as the lognormal curve shown in FIG. 18) can be satisfactorily estimated by varying bandwidth. In FIG. 18, panel A, a narrow bandwidth is chosen for good estimation of the mode. The small bandwidth, however, results in a very undersmoothed estimate of the tail of the curve. In FIG. 18, panel B, the larger bandwidth demonstrates a good estimate of the tail, but the mode is now oversmoothed. An intermediate bandwidth (FIG. 18, panel C) shows a more acceptable compromise between correct smoothing of the mode and the tail of the curve.

In flow cytometry, the measurement of the relative fluorescence of individual cells is summarized in a fine histogram of 256 or 1024 channels. For purposes of density estimation, these data are referred to as binned data. The kernel density estimate for binned data is provided by the equation in FIG. 19 (referred to henceforth as equation (1)), where $g^i$ is the $i^{th}$ bin center and $c^i$ is count for that bin. Bins correspond to channels for the flow cytometry data. Usually equation 1 is computed for x being set to each of the $g^i$'s. The result is a "smooth histogram" that is devoid of the aberrant features of the regional histogram.

An advantage of a kernel density estimate over a histogram is that derivatives of the underlying "true density function" are straightforward to obtain. A smoothed example of two actual flow cytometry histograms was shown in FIG. 14. The derivatives of these histograms showed measurable similarity. This is important for matching qualitative features between histograms. This feature is also crucial for the vectors used in the information retrieval system according to the invention. For example, the derivatives of the underlying density function can provide a measure of the location of the peaks and valleys as described above in relation to contour weighting. If k has a first derivative, as shown in FIG. 20, then the first density derivative can be estimated by differentiating equation (1), resulting in the function of FIG. 21. Zero-crossings of this function estimate the locations of peaks and valleys of the histogram. Inflection point of the histograms correspond to zero-crossings of the second density derivative. These functions can be estimated by further differentiation of equation (1), resulting in the equation of FIG. 22.

The choice of h needs to be reconsidered when estimating density derivatives: a bandwidth that is optimal for estimating the density is usually too small for good estimation of derivatives. Therefore, some increase in the bandwith is necessary for density estimation.

Strategies for data-driven choice of bandwith are described in Wand and Jones (P8). In the context of histogram analysis, bandwidth should be small enough to produce good resolution of the minor "peaks" and large enough to smooth technical artifacts. A strategy to identify artifactual peaks is the analysis of replicate samples. The peaks in the replicate samples believed to represent technical variance are analyzed and used to correct smoothing parameters.

Once the underlying true density function is obtained, a variety of analytic approaches can be applied. The derivative of the underlying density function is an example of an approach that can be used for matching qualitative features between histograms. It is anticipated that further refinements will allow us to not only accurately describe the qualitative features of histograms, but incorporate these data into the cumulative histogram database. The first and second density derivatives will define the location of the peaks, valleys and inflection points of the histograms. The definition of the ascending and descending slopes, weighted for their location, and the dispersion of the histogram are examples of other features to be included in the database of histogram descriptors.

Kernel estimators provide a number of practical and theoretical advantages in the development of a molecular knowledge base (see below). First, the accuracy of kernel estimators in defining the flow cytometry histograms is crucial to the development of effective knowledge discovery tools. The relationships defined in the knowledge base will be only as reliable as the histogram descriptors. The five-year pilot study suggests that most quantitative flow cytometry histograms will be sufficiently complicated to exclude the use of a simple parametric model. A kernel estimator, or preferably, two or more complementary kernel estimators can be incorporated into analytical algorithms in order to characterize flow cytometry histograms and provide a measure of "relatedness". The more similar the histograms, the more likely two monospecific probes recognize the same molecule. This similarity can be quantified and used to order the retrieval results from the database.

Web-Based Submission of Monospecific Probes

Investigators will be asked to contribute monospecific probes using a web-based submission form. Collecting the data on the web-based submission form provides both the contributing investigator and the reference laboratory with time-dated information. Preliminary experience suggests that the web-based submission form will minimize the confusion inherent in the numerous labeling conventions that are used for monospecific probes such as monoclonal antibodies. It can also insure that there is no pre-existing probe in the database with the same name. The web-based submission form will also improve communication by providing the contributing investigator with an e-mail confirmation as well as e-mail notification of the results when they are available.

Information requested on the Web-based submission form submitted with each monospecific probe will include, for example, the following (this listing is specific for Mab submissions; similar types of information regarding the source of a probe and anything known regarding its binding target will be requested for non-antibody probes such as aptamers):

1. A description of the immunogen.
2. The mouse strain and fusion partner.
3. The cells and tissues known to express the antigen by flow cytometry or immunohistochemistry.
4. The antibody isotype (if known).
5. The molecular weight of the target antigen (if known).

In the near-term, these procedural details will insure accurate data in the database. In the longer-term, information obtained from contributing investigators can be useful in drawing relevant biologic conclusions regarding the probes. For example, conclusions related to isotype frequencies, immunization protocols, and epitope frequencies of monoclonal antibodies can be drawn.

In addition, each submission must include at least two vials of frozen hybridoma cells (see flow diagram). In order to comply with import regulations, it can be necessary to require that probe-producing cells be grown under particular conditions before submission for inclusion in the database. For example, import regulations under an APHIS Import permit in the United States requires that the hybridoma cells are grown in fetal calf serum from an American supplier prior to freezing.

One of the vials submitted will be kept frozen as a backup and potential reference. The second vial will be thawed and expanded for in vitro testing. In the first several passages, the hybridoma cell line will be cryopreserved as additional backups.

Data Mining and Information Retrieval System

Data mining and information retrieval systems provide investigators with more than simply scaling up the basic process of histogram comparison. Information retrieval systems can be designed to be superior to visual inspection. In practice, histogram matching by visual inspection involves looking for a "perfect" match. When the investigator finds a striking similarity between monospecific probes in one cell type or subpopulation, other populations are compared to see if this similarity "holds-up." The discovery of any discrepancy between these monospecific probes argues against a common target molecule. In the typical situation, the original suspicion is immediately discarded. This process is repeated over and over. As the database grows, the likelihood that the investigator will revisit any of these possible associations is diminished. Further, the ability of the investigator to make comparisons by inspection decreases as the database grows. Thus, the investigator is overwhelmed and the potential cumulative value of the database is lost.

Looking for "striking similarity" when comparing histograms can also compromise the retrieval of monospecific probes that recognize the same molecule, but produce slightly different histograms. This can be the result of differences in antibody epitopes or binding affinity. Although the monospecific probes recognize the same molecule, they will produce similar, but not identical, patterns of reactivity. Investigators looking for a "perfect" match can prematurely disregard an association that a more systematic evaluation would identify.

Histogram comparison by inspection not only misses subtle differences, but also more complex patterns. Both the subtle and complex patterns of reactivity are currently lost in large histogram databases. A central design feature of the knowledge base developed according to the invention is an information retrieval system that recognizes these patterns.

The information retrieval system is designed to search for nuanced relationships between monospecific probes and for patterns of reactivity across cell types and subpopulations.

Figure 23:
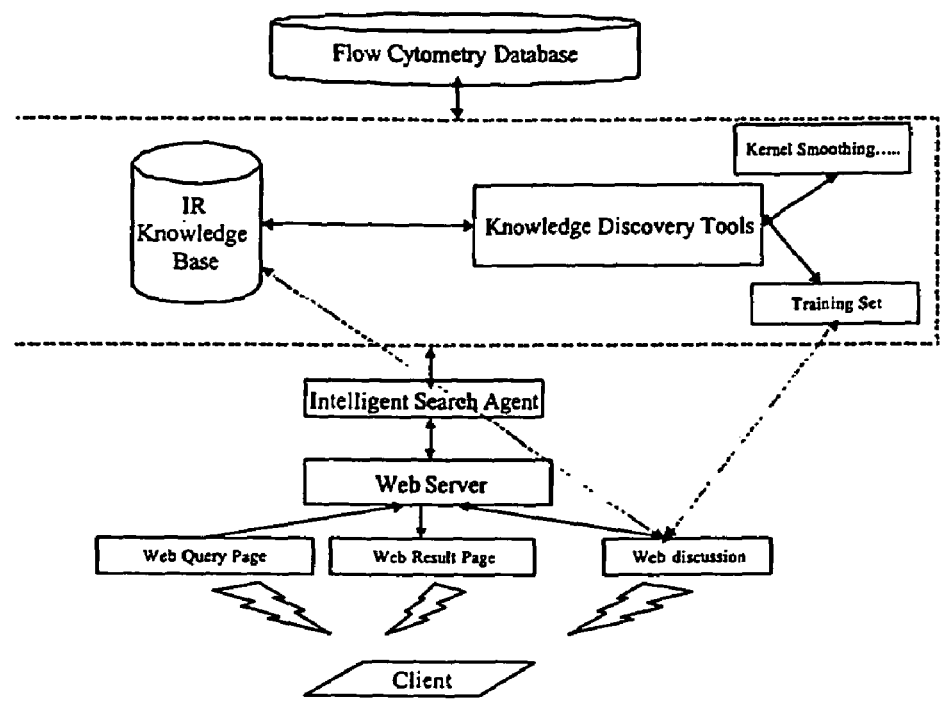
FIG. 23 shows a schematic of the functions and relationships of a database of the invention with respect to the information retrieval system and web-based client interface.

The information retrieval system according to the invention consists of a database, an information retrieval module that uses non-parametric approach(es) to data characterization, and a web server. The database will store the flow cytometry list mode files linked to a reference laboratory index. The web server will accept requests from investigators. In most cases, the investigators will request a molecular identification associated with a submitted monospecific probe. For example, the investigator can have submitted an undefined monoclonal antibody named ERD2/81. The query can ask the question "What is the target molecule recognized by the monoclonal antibody ERD2/81?" Alternatively, the investigator can query the relative similarity of two distinct monospecific probes: "Do the monoclonal antibodies ERD2/81 and T2/52 recognize the same molecule?" Once the request has been submitted, the information retrieval system conducts a knowledge-based information retrieval. The web server delivers these ranked results to the investigator. This process is shown schematically in FIG. 23.

A. Searching Techniques

Figure 24:
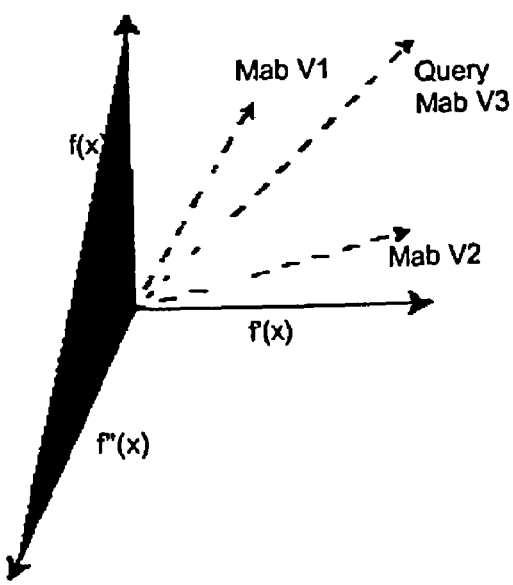
FIG. 24 shows a graphical representation of the relationships within the database between information about different monospecific probes.

Most current information retrieval algorithms are developed for querying textual documents by words or phrases. To effectively retrieve information from the molecular database, methods based on existing information retrieval and knowledge discovery techniques are used. FIG. 24 shows a graphical representation of the relationships within the database between information about different monospecific probes. Various approaches useful for searching the database of the invention are described below.

1. Feature Space Model. Kernel smoothing and density estimators allow us to recover structure in complex histograms. In many cases, the kernel functions can be represented by a definable metric; typically, a numerical value from 0 to 1 or 0 to 2. These mathematical "descriptors" can be incorporated into the molecular database stratified by cell type and subpopulations. Using multiple mathematical "descriptors," the histograms can be represented as vectors in high dimensional space. Each mathematical function, or dimension of the space model, will have an associated "weight." In the vector space retrieval model, weights are generally used to give emphasis to terms that provide meaning and utility to the retrieval. In standard text retrievals, the weights of the vector are first determined by how often a word appears in the document and how often it appears in all documents in the search space. In the molecular database, the weights of the vectors will first be assigned an equal value. In the vector space model using the genetic algorithms described below, several copies of the vector space would be created. The vectors within each vector space would be assigned random weights. A major focus of the knowledge base project will be the development of knowledge discovery algorithms to optimize these weights. A feature of database is the additional biochemical and genetic information will be available to test the validity of our matching algorithms over time. For example, additional testing may demonstrate that two antibodies recognize the same molecule. When this information is available, the results of our algorithm will be adjusted, using appropriate weighting, to produce the results obtained by external sources. A variety of mathematical, distance, and logical methods can be applied as knowledge discovery tools. An example is the nearest neighbor method which is currently being studied. As the histograms are represented in "feature" or "vector" space, the histograms can be clustered by proximity in this high-dimensional space. The similarities of the histograms would be predicted by their proximity. Alternatively, biologically important results may be identified not by similarity, but by dissimilarity. For example, reciprocal expression of two molecules may suggest reciprocal function. Also, parallel but nonidentical expression may suggest a similar functional relationship.

The basis for the mathematical "descriptors" used in the database will be reviewed and analyzed throughout the compilation of the database, and the growth of the knowledge base. An advantage of quantitative flow cytometry is that the vector space is relatively static. Given the accumulated knowledge in flow cytometry, and the extensive pilot study, the extent of the histograms vector space has been defined. This is a distinct advantage compared to textual retrieval systems which have to account for new ideas and expanding vocabularies. The disadvantage of the vector space is that the mathematical dimensions cannot be assumed to be orthogonal or independent. These relationships between mathematical dimensions will be defined empirically.

The similarity of histograms is assessed by traditional methods of statistical comparison such as independent and joint significance testing. For example, the similarity of histograms can be calculated based on their vectors spaces using standard statistical functions such inner product, Dice coefficient, cosine coefficient or the Jackard coefficient. Relevance testing can be used to refine this approach.

An alternative strategy in shaping the vector space retrieval model is the use of genetic algorithms. This retrieval strategy is based on an evolution of the vector space. The mechanisms of vector space evolution are reminiscent of the evolution of chromosomes. Multiple copies of the vector space are created: each with randomly assigned vector weights. The different vector spaces change with time according to programmable rules of inheritance, mutation and crossover. These rules function to create a computational evolution. The result of these changes in vector weights is that they either degrade or optimize the vector space. Depending on the definition of inheritance, mutation, and crossover in the system, it is possible that one can even develop entirely new vectors.

2. Relevance feedback. Relevance feedback is a process of refining the retrieval system using the results of a given query. After the results of a query are returned, the user indicates to the information retrieval system which aspects of the results are more relevant to the query. For textual documents, the system typically defines terms common to the "relevant" subset. These common terms are then added to the old query. The search is then repeated using the revised query. This process can be repeated as many times as desired.

In an information retrieval system useful in the invention, the query can be adjusted based on investigator feedback. Instead of adding common words, the system will modify the vector weights of "relevant" histograms. A classification algorithm (e.g. ID3) can be used to identify the most similar characteristics among the matching histograms. Using this process, additional weight is added to the selected "relevant" histograms. The similarity is then recalculated for the original query result. This process can be repeated and adjusted to bring the best match to the highest rank.

3. Training set. For feature selection and weight adjustment, a training set can be created. In the absence of a computational "gold standard," human experts will be necessary to define the relatedness of two histograms. As noted earlier in this specification, simple inspection of histograms is often sufficient to identify histogram relatedness. The challenge of the knowledge base will be scaling this process to a database consisting of thousands of histograms. To achieve this goal, a training set can be created and used to define the discovery tools.

To define the training set, a set of known matching histograms is collected. A second set of histograms is then randomly selected from the database. The two sets of histograms are then merged. This combined data set is then used for training. A panel of experts is then shown the training set. Histograms would then be judged pairwise by the panel as "most likely" related or "unlikely" to be related. The results of this training set can be used for feature selection in the analytic algorithm, as well as for weight adjustment in the vector space model. Feature selection includes peak location, valley location, inflection points, ascending and descending slopes as well as histogram dispersion.

Similar to the training set, a "testing set" can be created to assess feature selection and vector weights. A testing set will comprise, for example, previously defined CD molecules. In other words, the results of previous workshops can be used to identify known molecules and their defining monospecific probes. The known monospecific probes and the known relationships between them can be used to test the precision of the analytic model.

4. Performance measurement. The common performance measurements of information retrieval systems are precision and recall. Precision is defined as the number of relevant documents retrieved divided by the total number of documents retrieved. Precision is a measure of the specificity of the retrieval. Recall is defined as the number of relevant documents retrieved divided by the total number of relevant documents in the collection. Recall is a measure of the sensitivity of the retrieval. Our system will attempt to simultaneously maximize both recall and precision; however, it is not always possible to maximize both for the performance of each task. In some cases, the precision of the retrieval can be more important than recall. The scientific question can only require one specific answer. Alternatively, there can be situations in which the recall of the retrieval is more important. These situations can reflect more general scientific questions that require all the available data for their resolution. Preferably, one can maximize the performance of one measurement without compromising the other.

Another performance measurement will reflect standard utility measures. Utility measures generally assess how satisfied the user is with the performance of the information retrieval system. It is a distinct advantage in to have an active Advisory Board of experts in the field. The Advisory Board can provide direct feedback regarding the utility of the knowledge base. Other utility measures, such as user frequencies, can also be recorded and analyzed in order to monitor and improve the quality of the database and the knowledge base.

With the a reliable information retrieval system in place, each histogram added to the repository contributes to the database's cumulative value. As the number of histograms increases, and the number of monospecific probes increases, the value of the knowledge base will increase. This cumulative value is apparent, for example, when analyzing monospecific probes for features as straightforward as identical reactivity. Large numbers of virtually identical monospecific probes will help define the limits of statistical confidence. As mentioned previously, an important aspect of the database of the invention is that it will facilitate the identification of molecular patterns within the database. As more molecular families are analyzed, there will be increasing confidence in identifying complex patterns. The process of discovering these relationships and patterns (so-called "knowledge discovery") is achieved using informatics "tools" that will be applied to the histogram database.

The expanding size of the database, combined with evolving knowledge discovery tools, creates a potential problem for the investigator. Regardless of when the investigator "logs in" and requests the retrieval, the results are time-bound. The results will always be better the next day, or the next week. As the histogram database grows, the inspection process must be frequently repeated to avoid missing a potentially valuable comparison. For the individual investigator, the need to continually search the database is neither reassuring nor convenient.

B. Intelligent Search Agent

From the investigator's viewpoint, the ideal situation would be to submit a question to the knowledge base. For example, the investigator can query the knowledge base for the identity of the monoclonal antibody ERD2/81. The knowledge base might retrieve an immediate "preliminary" result. The question, however, would remain active in the knowledge base. The investigator would be updated by e-mail at intervals defined by the investigator, or when a definitive identity for the monoclonal antibody ERD2/81 is obtained. This function is provided by intelligent search agents. Intelligent search agents function as proxies for the investigator. The agents stay active to perform a task for the investigator over a definable time period. Not only is the data accumulated longitudinally, but the data can be retrieved longitudinally.

As the central component of the information retrieval system, these search agents are referred to as "intelligent" because they are designed to be capable of not simply matching identical histograms, but for identifying nuanced molecular relationships. These agents perform a "search" in the sense that they retrieve matches from the database and return the results. They are referred to as "agents" because they are acting on behalf of the investigator. A more subtle implication of "intelligent search agent" is that these agents will persist or be active in the knowledge base server until a solution is obtained. That is, an example of an intelligent search agent is a query that stays "active" or resident in memory until the question is resolved. The query may ask for a histogram "match" to a submitted monoclonal antibody that is at a confidence level>95 percent. This query will stay active until the match is obtained. At that point, the intelligent search agent will return the results (typically via e-mail). This feature is particularly important in an evolving molecular knowledge base.

C. Adaptive Retrieval

A unique feature of the molecular knowledge base is the participation of "expert" users. As evidenced by the Advisory Board, many of the investigators that will be using the molecular knowledge base are experienced at interpreting flow cytometry histograms. The retrieval system will exploit this training possibility. After seeing the initial results of the histogram retrieval, the investigator will have the option to provide feedback. The investigator can identify which histograms represent the better matches. The intelligent search agent will take this information and trigger the knowledge discovery tools. By combining investigator feedback with methods for knowledge discovery (e.g. mathematical, distance and logic methods) the system acquires new knowledge. This form of adaptive retrieval will improve the retrieval quality not only for that particular search request, but for future searches as well.

D. Group Retrieval

A theoretical possibility is that the intelligent search agents could be instructed to identify not only individual molecules, but entire molecular families. The process of group retrieval has the possibility of defining relationships between molecules and cell populations. The possibility of group retrieval is appealing because of the defined relationships of molecules in biologic systems. In our knowledge base, monospecific probes will define biomolecules by quantitative flow cytometry histograms. The flow cytometry histograms are then mathematically characterized and represented as vectors in the retrieval system (see below). From a theoretic viewpoint, the histograms are an intermediate representation of the molecules in biologic space and vector space. Because of this "direct relationship," it is plausible that molecular relationships that exist in biology might also be found in our vector space model. For example, the integrins are molecular families composed of alpha and beta subunits. The vector representation of these alpha and beta subunits are likely to uniquely define individual integrin molecular families. The patterns in these vector "clusters" can be useful in identifying molecules within these families as well as predicting new molecules or subunits.

E. Matching Alert

The intelligent search agents will provide investigators with an opportunity to have a continuous presence in the knowledgebase. Investigators can use intelligent search agents to delegate search tasks to be performed in a defined (or unlimited) time frame. For example, the investigator can be interested in the identity of the molecule defined by the ERD2/81 monoclonal antibody. The target molecule recognized by the monoclonal antibody ERD2/81, however, can not yet be identified. It can take multiple replicates or additional cell type or subpopulation analyses to define the identity of the target molecule. The ability of intelligent search agents to remain alert to these developments is an enormous practical advantage. It frees the investigator from the tedious task of multiple retrievals. It also ensures that molecular identification, once it has been defined, will be immediately communicated to interested investigators. This feature will not only be a convenience, but will hasten the pace of scientific investigations.

These design features, including knowledge discovery tools and intelligent search agents, will enhance the relevance of the knowledge base. Investigators will continually have updated information. The availability of this information will encourage monospecific probe submission. It will also encourage participation in knowledge base relevance testing and set training.

F. Web-Based Discussion

Finally, the information retrieval system useful in the invention comprises a Web server for accepting requests from investigators, accepting the submission of new monospecific probes, posting of new data, reassessing existing data and discussion threads.

The matching of histograms with defined molecular profiles will be the central focus of the knowledge base. There will be novel monospecific probes, however, that do not match any of the profiles in the existing knowledge base. In this case, the knowledge base will function to highlight the potential novelty of the monospecific probe. To facilitate the identification of the "unknown" target molecule, the Web site will provide investigators an opportunity to post new data, and reassess existing data, on an ongoing basis. Discussion threads will be started for each of the unknown antibodies. Members of the Advisory Board, as well as other investigators, will be invited to participate in the resolution of these unknowns. As each of these molecules is identified, the value of the knowledge base substantially increases.

The submission of several hundred hybridoma cell lines is anticipated. Because of the relatively stringent inclusion criteria, only 75 percent of the submitted hybridoma cell lines will be included in the molecular database. If each of the monoclonal antibodies derived from the hybridoma cell lines is tested against six to twelve cell types and subpopulations, this would create a primary database of approximately 2000 histograms. Replicate samples would increase this number to 10,000 to 15,000 histograms.

EXAMPLES

Example 1

A Molecular Knowledge Base of Mouse Anti-sheep Monoclonal Antibodies.

The molecular knowledge base is exemplified by a sheep model because it has been estimated that there are more murine Mab in sheep than in any nonhuman species. Also, the sheep model is active in such diverse experimental fields as immunology, cardiology and reproductive biology. Finally, sheep investigators have a well-established tradition of international cooperation and collaboration. Although the focus of this particular example is a database of anti-sheep monoclonal antibodies, the design principles defined in this application serve as a universal model for the development of a molecular knowledge base of monospecific probes recognizing binding targets in any species.

In order to establish a database of anti-sheep monoclonal antibodies the following steps are followed.

1. Using a Web-based Submission form, the investigator submitting an antibody provides the following information:

a) a description of the immunogen;

b) the mouse strain and hybridoma fusion partner;

c) the identity of cells and tissues known to express the antigen by flow cytometry or immunohistochemistry;

d) antibody isotype, if known; and e) the molecular weight of the target antigen, if known.

Along with the web-based submission, two vials of frozen hybridoma cells are submitted to the reference laboratory.

2. Upon receipt of the frozen cells and submission information, the reference laboratory performs the following:

a) One vial is thawed into culture and propagated in order to make sufficient stocks of secreted antibody for quality testing and flow cytometry analyses. The isotype and concentration of the antibody is determined, the hybridoma is screened for mycoplasma contamination, the cells are re-cloned to select clones with high production, and aliquots of antibody-containing hybridoma supernatant are frozen as stocks.

b) Quantitative flow cytometry is performed with the submitted antibody using a flow cytometer that has digital signal processing and which has been calibrated using three different calibration curves to accommodate small, medium and large cell types. Flow cytometry is performed on a panel of cell populations (or sub-populations) for each monospecific probe submitted. Each cytometry series includes a panel of known control (positive and negative) or reference monoclonal anti-sheep antibodies (or other known monospecific probes) specific to each individual cell population and defined by the reference laboratory.

c) The molecular weight of the target antigen is determined by immunoblotting, and the distribution of the antigen is evaluated by immunohistochemistry on a panel of tissues.

d) The flow cytometry data are characterized using parametric (and possibly non-parametric) approaches such as kernel smoothing, in order to closely estimate the "true density function" of that antibody's recognition profile on each cell type. The derivative of the estimated true density function is determined and used for computer comparison with those of flow cytometry data generated on the same flow cytometer, under essentially the same conditions, with other known or unknown antibodies or monospecific probes. The similarity of the smoothed profiles is assessed using standard statistical methods.

e) The smoothed flow cytometry profiles for the unknown antibody being characterized and information regarding monoclonal antibodies with similar cell population binding profiles are added to the database and made available on the web site.

In order for an investigator to determine whether there is a relationship between a monospecific probe of interest and others in the database, information concerning the mono specific probe of interest is submitted to the web site. The information submitted is compared to that in the monospecific probe information database, a list of matching monospecific probe information is generated, and the list is displayed in an order determined by the similarity of the information submitted by the user to that in the database. Investigators can provide input, in the form of relevance feedback and training set judgements, which are used to influence the weighting of various parameters in the intelligent search agents. The investigator input is thus applied to future analyses or comparisons of the data. This process can be performed on an ongoing basis (e.g., iteratively). Queries regarding unknowns are maintained actively within the knowledge base until the target of an unknown monospecific probe is identified. The intelligent search agents, combined with the standardized flow cytometry data generated by the reference laboratory and characterized by kernel smoothing and density estimators, permit data mining and the discovery of patterns within the data sets.

The following literature references contain information regarding hybridoma technology, kernel smoothing and kernel estimators, informatics and database development, and the leukocyte antigen database workshops. Each of the literature references referred to herein is incorporated herein in its entirety by reference.

Hybridoma Technology

P1. Li, X., K. Abdi, and S. J. Mentzer. 1992. Cloning hybridomas in a reversible three-dimensional alginate matrix. *Hybridoma*. 11:645–652.

P2. Abdi, K., X. Li, and S. J. Mentzer. 1993. Semi-dry PhastTransfer detection of biotinylated cell surface molecules. *Electrophoresis Journal*. 14:73–77.

P3. Li, X., K. Abdi, and S. J. Mentzer. 1994. o-phthaldehyde fluorescence microassay for the determination of antibody concentration. *J.Immunol.Methods*. 172:141–145.

P4. Li, X., K. Abdi, T. Herren, D. V. Faller, and S. J. Mentzer. 1994. Affinity membrane identification of immunoglobulin subclass in hybridoma screening. *Hybridoma*. 13:431–435.

P5. Li, X., K. Abdi, and S. J. Mentzer. 1995. Hybridoma screening using an amplified fluorescence microassay to quantify immunoglobulin concentration. *Hybridomna*. 14:75–78.

P6. Abdi, K., L. Kobzik, X. Li, and S. J. Mentzer. 1995. Expression of membrane glycoconjugates on sheep lung endothelium. *Lab.Invest.* 72:445–452.

P7. Su, M., C. He, C. A. West, and S. J. Mentzer. 2000. Generation of sheep x (sheep x mouse) heterohybridoma cell line expressing the beta 1 integrin membrane molecule. *Hybridoma*. In press.

Kernel Smoothing and Density Estimation

P8. Wand, M. P. and M. C. Jones. 1995. *Kernel Smoothing*. Chapman Hall, London.

P9. Hall, P., and M. P. Wand. 1988. On nonparametric discrimination using density differences. *Biometrika*. 75:541–547.

P10. Hardle, W., J. S. Marron, and M. P. Wand. 1990. Bandwidth choice for density derivatives. *Journal of the Royal Statistical Society*. 52:223–232.

P11. Wand, M. P. 1990. On exact L1 rates of convergence in non-parametric kernel regression. *Scandinavian Journal of Statistics*. 17:251–256.

P12. Carrol, R. J., and M. P. Wand. 1991. Semiparametric estimation in logistic measurement error models. *Journal of the Royal Statistical Society*. 53:573–585.

P13. Scott, D. W., and M. P. Wand. 1991. Feasibility of multivariate density estimates. *Biometrika*. 78:197–206.

P14. Wand, M. P., J. S. Marron, and D. Ruppert. 1991. Transformations in density estimation. Journal of the American Statistical Association. 86:343–361.

P15. Jones, M. C., and M. P. Wand. 1992. Effectiveness of some higher order kernels. Journal of Statistical Planning and Inference. 31:15–21.

P16. Marron, J. S., and M. P. Wand. 1992. Exact mean integrated squared error. The Annals of Statistics. 20:712–736.

P17. Ruppert, D., and M. P. Wand. 1992. Correcting for kurtosis in density estimation. Australian Journal of Statistics. 34:19–29.

P18. Wand, M. P. 1992. Finite sample performance of density estimators under moving average dependence. Statistics & Probability Letters. 13:109–115.

P19. Wand, M. P., and M. C. Jones. 1993. Comparison of smoothing parmeterizations in bivariate kernel density estimation. Journal of American Statistical Association. 88:520–528.

P20. Wand, M. P., and L. Devroye. 1993. How easy is a given density to estimate? Computational Statistics & Data Analysis. 16:311–323.

P21. Ruppert, D., and M. P. Wand. 1994. Multivariate locally weighted least squares regression. The Annals of Statistics. 22:1346–1370.

P22. Wand, M. P. 1994. Fast computation of multivariate kernel estimators. Journal of Computational and Graphical Statistic. 3:433–445.

P23. Wand, M. P., and M. C. Jones. 1994. Multivariate plug-in bandwidth selection. Computational Statistics. 9:97–116.

P24. Aldershof, B., J. S. Marron, and M. P. Wand. 1996. Facts about the gaussian probability density function. Applicable Analysis. 59:289–306.

P25. Aldershof, B., J. S. Marron, and M. P. Wand. 1995. Facts About the Gaussian Probability Density Function. Applicable analysis. 59:289–306.

P26. Fan, J., N. E. Heckman, and M. P. Wand. 1995. Local polynomial kernel regression for generalized linear models and quasi-likelihood functions. Journal of the American Statistical Association. 90:141–150.

P27. Herrmann, E., M. P. Wand, J. Engel, and T. Gasser. 1995. A bandwidth selector for bivariate kernel regression. Journal of the Royal Statistical Society. 57:171–180.

P28. Ruppert, D., S. J. Sheather, and M. P. Wand. 1995. An effective bandwidth selector for local least squares regression. Journal of the American Statistical Association. 90:1257–1270.

P29. Hall, P., and M. P. Wand. 1996. On the accuracy of binned kernel density estimators. Journal of Multivariate Analysis. 56:165–184.

P30. Manteiga, W. G., C. S. Sellero, and M. P. Wand. 1996. Accuracy of binned kernel functional approximations. Computational Statistics & Data Analysis. 31:1–16.

P31. Carroll, R. J., J. Fan, and M. P. Wand. 1997. Generalized partially linear single-index models. Journal of the American Statistical Association. 92:477–489.

P32. Hyndman, R. J., and M. P. Wand. 1997. Non-parametric autocovariance function estimation. Australian Journal of Statistics. 59:313–318.

P33. Ruppert, D., M. P. Wand, U. Holst, and O. Hossjer. 1997. Local polynomial variance-function estimation. Technometrics. 39:262–273.

P34. Wand, M. P. 1997. Data-based choice of histogram bin width. The American Statistician. 51:59–64.

Informatics and Database Development

P35. Greenes, R. A., R. C. McClure, E. Pattison-Gordon, and L. Sato. 1992. The findings—diagnosis continuum: implications for image descriptions and clinical databases. *Proc Annu Symp Comput Appl Med Care:*383–7.

P36. Greenes, R. A., M. Collen, and R. H. Shannon. 1994. Functional requirements as an integral part of the design and development process: summary and recommendations. *Int J Biomed Comput.* 34:59–76.

P37. Greenes, R. A. 1994. Strategic planning activities of the American Medical Informatics Association. *J Am Med Inform Assoc.* 1:263–71.

P38. Greenes, R. A. 1995. Informatics. *Acad Radiol.* 2 Suppl 2:S105–7.

P39. Greenes, R. A., and S. R. Deibel. 1995. Collaborative health care information system development through sharable infrastructure, services, and paradigms. *Medinfo.* 8:190–4.

P40. Shortliffe, E. H., G. O. Barnett, J. J. Cimino, R. A. Greenes, S. M. Huff, and V. L. Patel. 1996. Collaborative medical informatics research using the Internet and the World Wide Web. *Proc AMIA Annu Fall Symp:* 125–9.

P41. Greenes, R. A., A. Boxwala, and L. Ohno-Machado. 1999. The decision systems group: creating a framework for decision making. *MD Comput.* 16:23–7.

P42. Patel, V. L., D. R. Kaufman, V. G. Allen, E. H. Shortliffe, J. J. Cimino, and R. A. Greenes. 1999. Toward a framework for computer-mediated collaborative design in medical informatics. *Methods Inf Med.* 38:158–76.

P43. Shortliffe, E. H., V. L. Patel, J. J. Cimino, G. O. Barnett, and R. A. Greenes. 1998. A study of collaboration among medical informatics research laboratories. *Artif Intell Med.* 12:97–123.

P44. Zeng, Q., and J. J. Cimino. 1999. Evaluation of a system to identify relevant patient information and its impact on clinical information retrieval. *Proc AMIA Symp:*642–6.

P45. Zeng, Q., and J. J. Cimino. 1998. Automated knowledge extraction from the UMLS. *Proc AMIA Symp:* 568–72. P46. Zeng, Q., and J. J. Cimino. 1997. Linking a clinical system to heterogeneous information resources. *Proc AMIA Annu Fall Symp:*553–7.

P47. Cimino, J. J., G. Elhanan, and Q. Zeng. 1997. Supporting infobuttons with terminological knowledge. *Proc AMIA Annu Fall Symp:*528–32.

P48. Zeng, Q., and J. J. Cimino. 1996. Mapping medical vocabularies to the Unified Medical Language System. *Proc AMIA Annu Fall Symp:*105–9.

Leukocyte Antigen Database Workshops

P49. Naessens, J., C. J. Howard, and J. Hopkins. 1997. Nomenclature and characterization of leukocyte differentiation antigens in ruminants. *Immunol Today.* 18:365–8.

P50. Berthon, P., and J. Hopkins. 1996. Ruminant cluster CD14. *Vet Immunol Immunopathol.* 52:245–8.

P51. Gupta, V. K., I. McConnell, and J. Hopkins. 1993. Reactivity of the CD11/CD18 workshop monoclonal antibodies in the sheep. *Vet Immunol Immunopathol.* 39:93–102.

P52. Hopkins, J., A. Ross, and B. M. Dutia. 1993. Summary of workshop findings of leukocyte antigens in sheep. *Vet Immunol Immunopathol.* 39:49–59.

P53. Dutia, B. M., A. J. Ross, and J. Hopkins. 1993. Analysis of the monoclonal antibodies comprising WC6. *Vet Immunol Immunopathol.* 39:193–9.

P54. Dutia, B. M., A. J. Ross, and J. Hopkins. 1993. Comparison of workshop CD45R monoclonal antibodies with OvCD45R monoclonal antibodies in sheep. *Vet Immunol Immunopathol.* 39:121–8.

P55. Hopkins, J. 1991. Workshop studies on the ovine CD4 homologue. *Vet Immunol Immunopathol.* 27:101–2.

P56. Hopkins, J., and B. M. Dutia. 1991. Workshop studies on the ovine CD1 homologue. *Vet Immunol Immunopathol.* 27:97–9.

P57. Hein, W. R., L. Dudler, W. L. Marston, J. Hopkins, B. M. Dutia, K. Keech, M. R. Brandon, and C. R. Mackay. 1991. Summary of workshop findings for leukocyte antigens of sheep. *Vet Immunol Immunopathol.* 27:28–30.

P58. Dutia, B. M., and J. Hopkins. 1991. Analysis of the CD1 cluster in sheep. *Vet Immunol Immunopathol.* 27:189–94.

P59. Gupta, V. K., I. McConnell, R. G. Dalziel, and J. Hopkins. 1996. Identification of the sheep homologue of the monocyte cell surface molecule—CD14. *Vet Immunol Immunopathol.* 51:89–99.

P60. Gupta, V. K., I. McConnell, M. Pepin, W. C. Davis, R. G. Dalziel, and J. Hopkins. 1995. Biochemical and phenotypic characterization of the ovine beta 2 (leucocyte) integrins. *J Comp Pathol.* 112:339–49.

P61. Ballingall, K. T., B. M. Dutia, J. Hopkins, and H. Wright. 1995. Analysis of the fine specificities of sheep major histocompatibility complex class II-specific monoclonal antibodies using mouse L-cell transfectants. *Anim Genet.* 26:79–84.

P62. Dutia, B. M., I. McConnell, K. T. Ballingall, P. Keating, and J. Hopkins. 1994. Evidence for the expression of two distinct MHC class II DR beta like molecules in the sheep. *Anim Genet.* 25:235–41.

P63. Hopkins, J., and V. K. Gupta. 1996. Identification of three myeloid-specific differentiation antigens in sheep. *Vet Immunol Immunopathol.* 52:329–39.

The invention claimed is:

1. A system allowing users to obtain information on monospecific probes in an online directory comprising:
    a web site containing a database of monospecific probe properties, wherein said database comprises monospecific probe properties identified by flow cytometry, and wherein the information in the database comprises monospecific probe histograms, and connected to users through a computer network to allow users to enter selection criteria for retrieving monospecific probe properties;

wherein the web site produces a list of matching information on monospecific probes matching the selection criteria and displays the matching information on monospecific probes on the list in an order determined by each matching probe's similarity to the selection criteria.

2. The system of claim 1 wherein the histograms have been subjected to kernel smoothing or kernel density estimation.

3. The system of claim 1 wherein the order is determined by a technique selected from the group consisting of a feature space model, relevance feedback, set training, and performance measurement.

4. A method of providing information concerning monospecific probes to users through a web site, comprising the steps of:

receiving information relating a monospecific probe from a user;

comparing the information to a monospecific probe information database, wherein said database comprises monospecific probe properties identified by flow cytometry, and wherein the information in the database comprises monospecific probe histograms;

compiling a list of matching monospecific probe information matching the information relating to a monospecific probe received from a user; and displaying the matching monospecific probe information in an order determined by similarity of the information relating to a monospecific probe from a user to the monospecific probe information in the database.

5. The method of claim 4 further including the steps of receiving a monospecific probe from a user; and generating a histogram for the received monospecific probe by the same flow cytometer as the histograms generated for the monospecific probe whose information is contained in the information database.

6. The method of claim 5 wherein the histogram of the monospecific probe received from a user and the histograms of the monospecific probes contained in the database are subjected to kernel smoothing or kernel density estimation before comparison.

7. A directory computer containing a database, wherein said database comprises monospecific probe properties identified by flow cytometry, and wherein the information in the database comprises monospecific probe histograms, that permits users to obtain a list of monospecific probes matching selection criteria provided by the users through a web site hosted on the directory computer, wherein said directory computer displays matching monospecific probes matching the selection criteria in an order determined by each matching monospecific probe's similarity to the selection criteria.

8. The directory of claim 7 wherein the selection criteria is similarity of histograms.

9. The directory of claim 7 wherein the histograms have been subjected to kernel smoothing or kernel density estimation.

10. The directory of claim 7 wherein the order is determined by a technique selected from the group consisting of a feature space model, relevance feedback, set training, and performance measurement.

11. A computer readable medium having stored thereon computer-executable instructions for:

receiving selection criteria relating to information on a monospecific probe from a user;

compiling a list of matching monospecific probes matching the selection criteria from a database of monospecific probe information, wherein said database comprises monospecific probe properties identified by flow cytometry, and wherein the information in the database comprises monospecific probe histograms; and displaying the matching monospecific probe information in an order determined by each matching mono specific probe's similarity to the selection criteria.

12. The computer readable medium of claim 11 wherein the histograms have been subjected to kernel smoothing or kernel density estimation.

13. The computer readable medium of claim 11 wherein the order is determined by a technique selected from the group consisting of a vector space model, relevance feedback, training set, and performance measurement.

* * * * *